(12) United States Patent
Senoo et al.

(10) Patent No.: US 7,485,714 B2
(45) Date of Patent: Feb. 3, 2009

(54) TRANSCRIPTION FACTOR HAVING ZINC FINGER DOMAIN

(75) Inventors: Chiaki Senoo, Gotenba (JP); Mariko Numata, Ibaraki (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 221 days.

(21) Appl. No.: 10/312,680

(22) PCT Filed: Jun. 14, 2001

(86) PCT No.: PCT/JP01/05066

§ 371 (c)(1), (2), (4) Date: Apr. 28, 2003

(87) PCT Pub. No.: WO01/98492

PCT Pub. Date: Dec. 27, 2001

(65) Prior Publication Data

US 2003/0162205 A1 Aug. 28, 2003

(30) Foreign Application Priority Data

Jun. 20, 2000 (JP) ............................. 2000-189762

(51) Int. Cl.
| | |
|---|---|
| C07H 21/04 | (2006.01) |
| C12N 15/63 | (2006.01) |
| C12N 15/85 | (2006.01) |
| C12N 15/86 | (2006.01) |
| C12P 21/00 | (2006.01) |

(52) U.S. Cl. ................... 536/23.5; 435/320.1; 435/325; 435/70.1

(58) Field of Classification Search ........................ None
See application file for complete search history.

(56) References Cited

U.S. PATENT DOCUMENTS

| | | | |
|---|---|---|---|
| 5,288,607 A | * | 2/1994 | Emorine et al. ............... 435/6 |
| 5,807,678 A | * | 9/1998 | Miller et al. ................... 435/6 |
| 5,831,008 A | | 11/1998 | Huang et al. |
| 6,008,048 A | * | 12/1999 | Monia ........................ 435/375 |

FOREIGN PATENT DOCUMENTS

WO WO-98/02455 1/1998

OTHER PUBLICATIONS

Whisstock et al. Predicition of protein function from protein sequence and structure. Q Rev Biophys. 2003 vol. 36(3) pp. 307-340.*
GenBank Accession No. AW303983 GI 6713672 Entered Jan. 18, 2000.*
Williams, Gregg et al. E1a Transactivation of the human HSP70 promoter is mediated through the basal transcriptional complex. 1989. Molecular and Cellular Biology. vol. 9. No. 6. pp. 2574-2587.*
GenBank Accession No. AC007405.3 GI 7631078, Apr. 21, 2000.*
Harrison et al. Sp5, a New Memeber of the Sp1 Family, Is Dynamically Expressed during Development and Genetically Interacts with Brachyury. 2000. Developmental Biology. vol. 227 pp. 358-372. See also Accession No. AF279479.*
Waterson et al. The sequence of *Homo sapiens* clone. 1999. Genome Sequencing Center, Washington University School of Medicine. See Accession No. AC007405.1 version GI:4680771.*
Database EMBL, accession No. AL033342 (1999).
Database EMBL, accession No. AI275629 (1998).
Supplementary Partial European Search Report for EP 01938663.0, mailed on Jan. 16, 2006, 5 pages.
Cook et al., Annals of the New York Academy of Sciences (1999) 880(1):94-102.
Courey et al., Cell (1988) 55:887-898.
Dynan et al., Cell (1983) 35:79-87.
Gidoni et al., Nature (1984) 312:409-413.
Habara-Ohkubo, Cell Struct. Funct. (1996) 21(2):101-110.
Hagen et al., EMBO J. (1994) 13:3843-3851.
Hagen et al., Nucleic Acids Res. (1992) 20:5519-5525.
Harrison et al., Dev. Biol. (2000) 227(2):358-372.
Imataka et al., EMBO J. (1992) 11(10):3663-3671.
Kadonaga et al., Cell (1987) 51:1079-1090.
Kingsley et al., Mol. Cell Biol. (1992) 12:4251-4261.
Philipsen et al., Nucleic Acids Res. (1999) 27:2991-3000.
Zhu et al., Mol. Cell. Biol. (1993) 13(7):4432-4444.
Luu and Flores, Journal of Virology (1997) 71(9):6683-6691.
Scohy et al., Genomics (2000) 70:93-101.
Treichel et al., Mechanisms of Development (2001) 101:175-179.

* cited by examiner

*Primary Examiner*—Ram R. Shukla
*Assistant Examiner*—Amanda Shaw
(74) *Attorney, Agent, or Firm*—Morrison & Foerster LLP

(57) ABSTRACT

Using an undifferentiated mouse CL6 cell line, DMSO was added to induce its differentiation into cardiac muscular cells in order to obtain gene fragments whose expression elevated upon the induction. The isolated gene had zinc finger domains and showed a significant homology to the Sp1 family genes. Furthermore, a human gene corresponding to this mouse gene was isolated. The protein encoded by this gene existed in the nucleus and bonded to a GC-box. The protein was revealed to repress the transcription regulatory activity of the CMV promoter and thus serves as a transcription factor.

6 Claims, 12 Drawing Sheets

FIG. 1

```
AGCTTGGGCCCCTCGAGGGATCCTCTAGAGCGGCCGCCYYCTGCTCCACAGCGAGCGGCCTTCAAGCAGTAGCCATGGCCGCTGTGGCCG   90
                                                                        M  A  A  V  A  V

TCCTCCGGAACGACTCACTGCAGGCCTTCCTCCAGGACCGCACCCCCAGCGCCTCCCCGGACCTGGGCAAGCACTCGCCCCTGGCGCTGC  180
 L  R  N  D  S  L  Q  A  F  L  Q  D  R  T  P  S  A  S  P  D  L  G  K  H  S  P  L  A  L  L

TGGCCGCCACCTGTAGCCGGATCGGCCAGCCCGGCGCTGGGCGGCACCCGACTTCCTTCAGGTGCCCTATGACCCAGCGCTGGGTTCAC  270
 A  A  T  C  S  R  I  G  Q  P  G  A  A  A  A  P  D  F  L  Q  V  P  Y  D  P  A  L  G  S  P

CCTCCAGACTTTTCCACCCTTGGACTGCCGACATGCCCGCGCACTCGCCAGGCGCCCTGCCGCCCCCACACCCCAGCTGGGCTGACGC  360
 S  R  L  F  H  P  W  T  A  D  M  P  A  H  S  P  G  A  L  P  P  P  H  P  S  L  G  L  T  P

CGCAGAAAACACACCTGCAGCCGTCCTTCGGGCAGCCCACGAGCTCCCGCTCACGCCCCCGCGGATCCGTCGTACCCTTACGAGTTCT  450
 Q  K  T  H  L  Q  P  S  F  G  A  A  H  E  L  P  L  T  P  P  A  D  P  S  Y  P  Y  E  F  S

CGCCGGTCAAGATGCTGCCCTCGAGCATGGCTGCTCTGCCTGCCAGCTGCGCGCCCGCCTACGTGCCCTACGCCGCGCAGGCCGCGTTGC  540
 P  V  K  M  L  P  S  S  M  A  A  L  P  A  S  C  A  P  A  Y  V  P  Y  A  A  Q  A  A  L  P

CCCCGGGCTACTCCAACCTGCTGCCCCCGCCGCCGCCACCGCTTCCACGCCCACCTGCCGCCAGTTATCCCCGCCCCGGCTCCGGACG  630
 P  G  Y  S  N  L  L  P  P  P  P  P  P  P  P  P  P  T  C  R  Q  L  S  P  A  P  A  P  D  D

ACCTCCCCTGGTGGAGCATCCCGCAATCGGGCGCGGGGCCGGGAGCTCCGGGGTTCCAGGGACCAGCCTCTCCAGCGCCTGTGCCGGAC  720
 L  P  W  W  S  I  P  Q  S  G  A  G  P  G  S  S  G  V  P  G  T  S  L  S  S  A  C  A  G  P

CTCCCCACGCTCCCCGCTTCCCTGCCTCAGCCGCCGCTGCTGCAGCGGCGGGCTGCTGCCCTGCAACGGGGTCTAGTGTTGGGCCCGTCGG  810
 P  H  A  P  R  F  P  A  S  A  A  A  A  A  A  A  A  A  A  A  L  Q  R  G  L  V  L  G  P  S  D

ACTTTGCACAGTACCAGAGCCAGATCGCCGCGCTGCTGCAGACCAAGGCCCCCCTGGCGGCCACGGCCAGGAGGTGCCGCCGCTGCCGCT  900
 F  A  Q  Y  Q  S  Q  I  A  A  L  L  Q  T  K  A  P  L  A  A  T  A  R  R  C  R  R  C  R  C

GCCCCAACTGCCAGGCGGCTGGCGGTGCCCCGAGGCGGAACCGGGCAAAAAGAAGCAACACGTGTGCCACGTGCCAGGCTGTGGCAAGG  990
 P  N  C  Q  A  A  G  G  A  P  E  A  E  P  G  K  K  K  Q  H  V  C  H  V  P  G  C  G  K  V

TGTACGGCAAAACGTCGCACCTGAAGGCGCACCTGCGCTGGCACACGGGCGAGCGGCCCTTCGTGTGCAACTGGCTCTTCTGCGGCAAGA 1080
 Y  G  K  T  S  H  L  K  A  H  L  R  W  H  T  G  E  R  P  F  V  C  N  W  L  F  C  G  K  S

GCTTCACGCGCTCGGACGAGCTGCAACGGCACCTGCGGACTCACACGGGCGAGAAGCGCTTCGCTTGTCCCGAGTGCGGCAAACGCTTCA 1170
 F  T  R  S  D  E  L  Q  R  H  L  R  T  H  T  G  E  K  R  F  A  C  P  E  C  G  K  R  F  M

TGCGAAGCGATCACCTCGCCAAGCACGTGAAGACGCACCAAAATAAGAAGCTCAAAGTCGCTGAGGCCGGGGTGAAGCGGGAGAATCCGC 1260
 R  S  D  H  L  A  K  H  V  K  T  H  Q  N  K  K  L  K  V  A  E  A  G  V  K  R  E  N  P  R

GGGACCTATGAGCGCACCGGGACACTTTCGAGGCCACTCCTGCCCAAGACATCTTTCCCAGCACCTTTGCTGGCACACCAGGGTACTTGC 1350
 D  L

CATCGAGGTAGCTGACAAAGAGTAACTTTTTAAATGAACTTTTTATTCTCCTCCGCCCGAAGTCTTGCTGTCCAGCCCAAGAGCAGAGGG 1440

CAGGGCAGGCAGGACAGGAAACTGGGTCGTAGTTGAGTTACCCCAGGAGGATTCCAAAGTCCGAGCCATCGCTGCCTGGGAGACTTACA  1530

TTTTACCCAGGGCTGGCCTTGCTTGTGGGAGTCGCTGCTGAAAAAAAATTTTAAAAAGAAGGCTCTTGGGAGATTTAAAAACAAGGCCTA 1620

AGTTTTTGCTAGGCCCGATTCGGACTTTGTACAGGTTATTTAATAATAGCTTTGTTAAAGAGTAATTATGATTATAACGTTAATAAATGT 1710

TTCTGTTGTTCTCAGCTCCACGCAGAGCTACAGCATGGTACGTTTCTGTAAAGCGAACAGCAGTTGGCAGCGTGAAAATAAATACTTCAT 1800

TCCAGGGTCTCCTCGGGAAGACCCCCACAG  1830
```

FIG. 2

| | | | | |
|---|---|---|---|---|
| Sp1-Hu ZF | CHIQGCGKVYGKTSHLRAH | LRWHTGERPFMCTWSYC | GKRFTRSDELQRH | TGEKKFACPECPKRFMRSDHLSKHIKTH |
| Sp2-Hu ZF | ---PD---------L---- | ----V-L---------- | ---------------A- | -------D-R-E-AQ-Q------T--Y- |
| Sp3-Hu ZF | ---P--------------- | S---V-N-FF------- | ---------------R- | ----------V----S-------A---- |
| Sp4-Hu ZF | ---E--------------- | ----I-N-MF------- | ---------------R- | -------R-E----S---------V--- |
| m285 ZF | -VP---------K------ | ----V-N-LF----S-- | ---------------L- | -------R-------G-------A-V-- |
| BTEB1-Hu ZF | PYS---------S---Y-V | ---PD-L-KS-----T- | ---------------Y- | -------Q-R-L-E---------T-ARR |
| BTEB3-Ms ZF | -YA-E-------K---T-- | A-S-QE-N-K-A---A- | ---------------Y- | -------S-I-E----------T-ARR |
| TIEG1-Hu ZF | SHP--T-F-S--K---T-T | K-S-S-KG-ER---A-- | ---------------S- | -------V--M-DR---------T-ARR |
| TIEG2-Hu ZF | SFP-R-T-F-S--K---T- | K-N-S-DG-D-K-A--- | ---------------S- | -------V--V-DR---------T-ARR |
| EKLF-Hu ZF | AHP--S-T-S--K---T-- | K-YA---EG-W--A--- | ---------------T- | -Y-K---QRP-R-QL--RA-S----AL-M-R |
| GKLF-Hu ZF | DYA--T-T-S--K---T-- | K-YH-D-DG-WK-A--- | ---------------T- | -Y-K---HRP-Q-QK--DRA-S----AL-M-R |
| LKLF-Hu ZF | SYA--T-T-S--K---T-- | K-YH-N-DG-WK-A--- | ---------------T- | -Y-K---HRP-Q-HL--DRA-S----AL-M-R |
| ZNF741-Hu ZF | DFA-S---T-S--K--R-I | K-YK---DG-SWK-A-- | ---------------T- | -F-K---I-P-R-TD--NRS-S----L-RRR |
| BKLF-Hu ZF | DYD-N---T-S--K--R-T | K-YK---EG-TWK-A-- | ---------------T- | -F-K---I-P-Q---D-DRS-S----AL-M-R |
| IKLF-Hu ZF | DYP-T---T-S--K---T- | K-YK---EG-DW--A-- | ---------------T- | -Y-K---A-P-Q-GV--NRS-S----AL-M-R |
| BTEB2-Hu ZF | DYP-T---T-S--K---T- | K-YK---EG-DW--A-- | ---------------T- | -Y-K---A-P-Q-GV--NRS-S----AL-M-R |
| ZF9-Hu ZF | -FN-R---T-S--K--Q-T | K-YR-S-EG-EW--A-- | ---------------T- | -F-K---A-P-K-SH--DRC-S----GL-M-R |
| UKLF-Hu ZF | QFN-R---T-S--K--Q-T | K-YK-S-EG-EW--A-- | ---------------T- | -Y-K---A-P-K-NH--DRC-S----AL-M-R |

FIG. 3

```
SP1-Ms  11  VTAVVKIEKDVGGNNGGSGNGGAAFSQTRSSSTGSSSSGGGGGESQPSPLALLAATCSRIESPNENSNNSQGPSQSG  90
Sp2-Hu   1  ----------------------------MAATAAVSPSDYLQPAASTTQDSQPSPLALLAATCSKIGPPAVEAAVTPPAPQP  55
Sp4-Hu   1  ----MSDQKKEEEEAAAAAMATEGGKTSEPENNNKKPKTSGSQDSQPSPLALLAATCSKIGTPGENQATGQQQIID  75
m285     1  ---------------MAAVAVLRNDSLQAFLQDRTPSASPDLGKHSPLALLAATCSRIGQPGAAAAPDFLQVPYD  60
```

FIG. 4
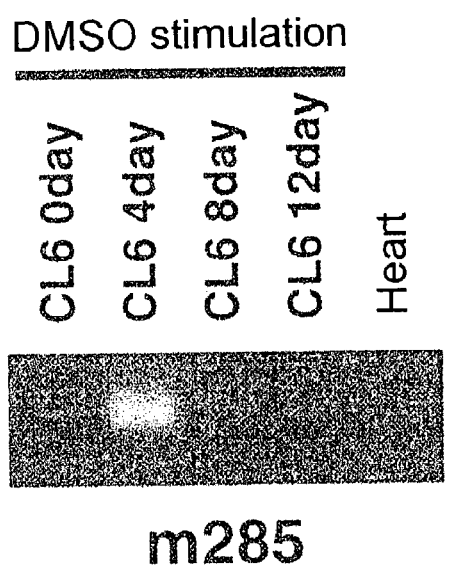
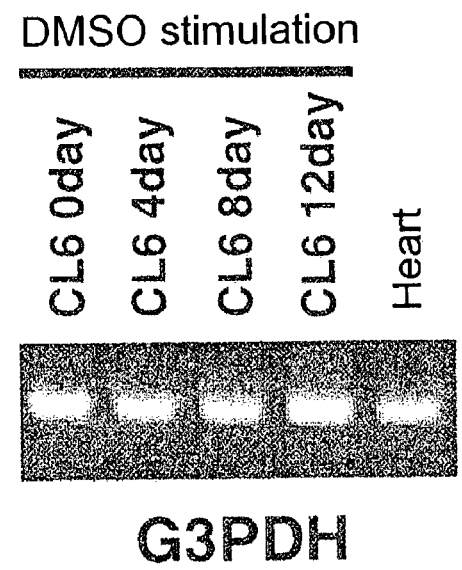

FIG. 6

```
ATGGCCGCGGTGGCCGTCCTCCGGAACGACTCGCTGCAGGCCTTTCTCCAGGACCGGACCCCCAGCGCCTCCCCGGACCTGGGCAAGCAC  90
 M  A  A  V  A  V  L  R  N  D  S  L  Q  A  F  L  Q  D  R  T  P  S  A  S  P  D  L  G  K  H

TCGCCCCTGGCCATTGCTGGCCGCCACCTGTAGCCGCATCGGCCAGCCGGGCGCGGCGGCGCCCCCGGACTTCCTGCAGGTGCCCTACGAC  180
 S  P  L  A  L  L  A  A  T  C  S  R  I  G  Q  P  G  A  A  A  P  P  D  F  L  Q  V  P  Y  D

CCCGCGCTGGGCTCACCCTCCAGGCTCTTCCACCCGTGGACCGCCGACATGCCGGCGCACTGGCCAGGCGCACTGCCGCCCCCGCATCCC  270
 P  A  L  G  S  P  S  R  L  F  H  P  W  T  A  D  M  P  A  H  S  P  G  A  L  P  P  P  H  P

AGCTTGGGGCTGACGCCGCAGAAGACGCACCTGCAGCCGTCCTTGGGGCTGCGCACGAGCTTCCCCTTACACCCCCCGCCGACCCCTCG  360
 S  L  G  L  T  P  Q  K  T  H  L  Q  P  S  F  G  A  A  H  E  L  P  L  T  P  P  A  D  P  S

TACCCCTACGAGTTCTCGCCGGTCAAGATGCTGCCCTCGAGCATGGCGGCTCTGCCCGCCAGCTGCGCGCCCGCCTACGTGCCCTACGCG  450
 Y  P  Y  E  F  S  P  V  K  M  L  P  S  S  M  A  A  L  P  A  S  C  A  P  A  Y  V  P  Y  A

GCGCAGGCCGCGCTGCCGCCAGGCTACTCCAACCTGCTGCCTCCGCCGCCGCCACCGCCCCCGCCGCCCACCTGCCGCCAGTTGTCACCC  540
 A  Q  A  A  L  P  P  G  Y  S  N  L  L  P̲  P̲  P̲  P̲  P̲  P̲  P̲  P̲  P̲  P̲  P̲  T  C  R  Q  L  S  P

AACCCGGCCCCCGACGACCTCCCGTGGTGGAGCATCCCGCAGGCGGGCGCCGGCCGGGGGGGCCTCCGGGGTTCCGGGAAGCGGCCTCTCC  630
 N  P  A  P  D  D  L  P  W  W  S  I  P  Q  A  G  A  G  P  G  A  S  G  V  P  G  S  G  L  S

GGCGCCTGTGCCGGGGCCCCCCACGCGCCCCGCTTCCCCGCCTCTGCGGCCGCTGCTGCTGCGGCCGCCGCCGCCCTACAAAGAGGCCTG  720
 G  A  C  A  G  A  P  H  A  P  R  F  P  A  S  A̲  A̲  A̲  A̲  A̲  A̲  A̲  A̲  A̲  A̲  L  Q  R  G  L

GTGTTGGGCCCGTCGGACTTTGCGCAGTACCAGAGCCAGATCGCCGCGCTGCTGCAGACCAAGGCCCCCCTGGCGGCCACGGCCAGGAGG  810
 V  L  G  P  S  D  F  A  Q  Y  Q  S  Q  I  A  A  L  L  Q  T  K  A  P  L  A  A  T  A  R  R

TGCCGCCGCTGCCGCTGTCCCAACTGCCAGGCGGCGGGCGGCGCCCCCGAGGCGGAGCCGGGGAAGAAGAAGCAGCACGTGTGCCACGTG  900
 C  R  R  C  R  C  P  N  C  Q  A  A  G  G  A  P  E  A  E  P  G  K  K  K  Q  H  V  C  H  V

CCCGGCTGCGGCAAGGTGTACGGGAAGACGTCGCACCTGAAGGCGCACCTGCGCTGGCACACGGGCGAGCGACCCTTCGTGTGCAACTGG  990
 P  G  C  G  K  V  Y  G  K  T  S  H  L  K  A  H  L  R  W  H  T  G  E  R  P  F  V  C  N  W

CTCTTCTGCGGGAAGAGCTTCACGCGCTCGGACGAGCTGCAGCGGCACCTGCGGACTCACACGGGCGAGAAGCGCTTTGCCTGTCCCGAG  1080
 L  F  C  G  K  S  F  T  R  S  D  E  L  Q  R  H  L  R  T  H  T  G  E  K  R  F  A  C  P  E

TGCGGCAAGCGCTTCATGCGCAGCGACCACCTGGCGAAGCACGTCAAGACTCACCAGAATAAGAAGCTCAAAGTCGCTGAGGCCGGGGTT  1170
 C  G  K  R  F  M  R  S  D  H  L  A  K  H  V  K  T  H  Q  N  K  K  L  K  V  A  E  A  G  V

AAGCGGGAGGACGCGCGGGACCTGTGA  1197
 K  R  E  D  A  R  D  L  *
```

FIG. 7

```
m285    1'  MAAVAVLRNDSLQAFLQDRTPSASPDLGKHSPLALLAATCSRIGQPGAAAAPDFLQVPYD
            ************************************************.*********
h285    1"  MAAVAVLRNDSLQAFLQDRTPSASPDLGKHSPLALLAATCSRIGQPGAAAPPDFLQVPYD m285   61'  PALGSPSRLFHPWTADMPAHSPGALPPPHPSLGLTPQKTHLQPSFGAAHELPLTPPADPS
            ************************************************************
h285   61"  PALGSPSRLFHPWTADMPAHSPGALPPPHPSLGLTPQKTHLQPSFGAAHELPLTPPADPS m285  121'  YPYEFSPVKMLPSSMAALPASCAPAYVPYAAQAALPPGYSNLLPPPPPPPPPPTCRQLSP
            ************************************************************
h285  121"  YPYEFSPVKMLPSSMAALPASCAPAYVPYAAQAALPPGYSNLLPPPPPPPPPPTCRQLSP m285  181'  APAPDDLPWWSIPQSGAGPGSSGVPGTSLSSACAGPPHAPRFPASAAAAAAAAAAALQRGL
            .**********.*.*...**.***********************
h285  181"  NPAPDDLPWWSIPQAGAGPGASGVPGSGLSGACAGAPHAPRFPASAAAAAAAAAAALQRGL m285  241'  VLGPSDFAQYQSQIAALLQTKAPLAATARRCRRCRCPNCQAAGGAPEAEPGKKKQHVCHV
            ************************************************************
h285  241"  VLGPSDFAQYQSQIAALLQTKAPLAATARRCRRCRCPNCQAAGGAPEAEPGKKKQHVCHV m285  301'  PGCGKVYGKTSHLKAHLRWHTGERPFVCNWLFCGKSFTRSDELQRHLRTHTGEKRFACPE
            ************************************************************
h285  301"  PGCGKVYGKTSHLKAHLRWHTGERPFVCNWLFCGKSFTRSDELQRHLRTHTGEKRFACPE m285  361'  CGKRFMRSDHLAKHVKTHQNKKLKVAEAGVKRENPRDL
            *******************************..*
h285  361"  CGKRFMRSDHLAKHVKTHQNKKLKVAEAGVKREDARDL
```

TRANSCRIPTION FACTOR HAVING ZINC FINGER DOMAIN

Reference To Sequence Listing Submitted Via EFS-WEB

The entire content of the following electronic submission of the sequence listing via the USPTO EFS-WEB server, as authorized and set forth in MPEP § 1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 532842000500Seqlist.txt | Jan. 29, 2008 | 30,474 bytes |

TECHNICAL FIELD

The present invention relates to novel proteins with zinc finger domains that bind to a GC-box, genes encoding these proteins, as well as production and use of these proteins and their genes.

BACKGROUND ART

G-rich elements, such as GC-box or GT-box, are sequences that bind to transcription factors which have been found in promoter sequences of various genes including house keeping genes as well as tissue specific genes, parentally expressing genes, etc. The G-rich elements are closely related to development and differentiation, in addition to gene expression upon the binding of transcription factors.

Sp1 has been found as a DNA-binding transcription factor that binds to the GC-box of the SV-40 promoter sequence to regulate the transcriptional activity of the promoter (Dynan W S. et al. (1983) Cell 35, 79-87; Gidoni D. et al. (1984) Nature 312, 409-13). The Sp1 has three zinc finger domains in its C-terminal region and binds to a GC/GT-box through the domains (Kadonaga J T. et al. (1987) Cell 51, 1079-90). Moreover, it has been known that the Sp1 has two glutamine-rich regions required for the activation of transcription (Courey A J. et al. (1988) Cell 55, 887-98), and yet two serine/threonine-rich regions. Transcription factor homologues, Sp2 (Kingsley C. et al. (1992) Mol Cell Biol 12, 4251-61), Sp3, and Sp4 (Hagen G. et al. (1992) Nucleic Acids Res 20, 5519-25), with a high homology to the Sp1 are known to exist and they comprise a family. Each transcription factor has three highly conserved zinc finger domains in its C-terminal region, and besides, a glutamine-rich region and/or a serine/threonine-rich region. While the Sp3 and Sp4, similarly to the Sp1, bind to a GC/GT-box (Hagen G. et al. (1992) Nucleic Acids Res. 20, 5519-25; Hagen G. et al. (1994) EMBO J 13, 3843-51), the Sp2 is reported not to bind to a GC-box and rather binds to a GT-box in the Vα promoter region of TCR (Kingsley C. et al. (1992) Mol. Cell. Biol. 12, 4251-61).

Recently, many transcription factors with high homology to the three zinc finger domains of Sp1 have been reported (Philipsen S. et al. (1999) Nucleic Acids Res. 27, 2991-3000). As in the case with Sp1, they all have been shown to have three zinc finger domains in its C-terminal regions and bind to a GC/GT-box; however, other regions share only a low homology with the Sp-family and do not have a glutamine-rich region that functions as a transcription activation region in Sp1.

These GC/GT-box binding transcription factors have been known to enhance or repress the transcriptional activity, and thus, are considered to regulate gene expression in various cells during development, differentiation, and such. Such characteristics of the GC/GT-box binding transcription factors described above presently make them remarkable as targets in developing therapeutic agents.

DISCLOSURE OF THE INVENTION

The present invention provides novel proteins with zinc finger domains that bind to a GC-box, genes encoding the proteins, and molecules functionally equivalent thereto, as well as production and use thereof.

The present inventors searched for genes whose expression increases in response to the differentiation of the mouse CL6 cell, for which a system to induce differentiation to cardiomyocyte-like cell by DMSO addition has been established, to discover genes involved in cardiac muscle differentiation.

First, the present inventors conducted the subtraction method using polyA+ RNA prepared from undifferentiated CL6 cells and those 4 days after DMSO addition, and obtained many gene fragments whose expression had been increased upon the induction of differentiation. One clone among them, clone PS40-285, was revealed to be a novel gene with zinc finger domains by a homology search and amino acid sequence motif search. Accordingly, cloning of a cDNA comprising the whole ORF of the novel gene was carried out and its nucleotide sequence was determined.

As a result, the protein encoded by the novel murine gene (m285) was identified as a protein consisting of 398 amino acids with three zinc finger motifs. These three zinc finger domains were located near its C-terminus and the sequence showed high homology with the three zinc finger domains of known SP family transcription factors (SP1, 2, 3, and 4). Further, a region near the N-terminus was also found to share a high homology with SP1, 2, and 4. Other regions of the protein showed no high homology with known genes.

Next, m285 gene expression during the differentiation-inducing process of CL6 cells by DMSO stimulation was examined to reveal a transient expression of the gene 4 days after the induction of differentiation. Moreover, tissue distribution analysis of the gene expression by the Northern blot analysis revealed that m285 is very highly expressed in 17 days postcoitum (dpc) murine embryo and almost no expression could be observed in 7 dpc, 11 dpc, and 15 dpc embryos. However, in adult tissues, expression of the gene in testicular tissue was observed, but it was weakly expressed in brain, heart, liver, and kidney.

The present inventors also cloned a cDNA containing the total ORF of the novel human gene (h285), which is the human counterpart of m285. The h285 encoded 398 amino acids, which is the same as m285. According to the comparison of the obtained h285 to m285, it had a homology of 91.1% at the nucleotide sequence level within the coding region, and 97.5% homology at the amino acid sequence level.

Transcription factors are generally localized in the nucleus. Thus, the cellular distribution of m285 was analyzed. As a result, m285 was revealed to exist in the nucleus and the C-terminal region including three zinc finger domains was required for its nuclear translocation. Moreover, according to a DNA binding assay, m285 was revealed to bind to the nucleotide sequence of a GC-box, identical to the SP family transcription factors, at its C-terminal region that include the three zinc finger domains. The GC-box is known to exist in the promoter/enhancer regions of many genes. According to these facts, gene 285 is expected to regulate the transcription of genes through the binding to a GC-box.

Then the mode of transcriptional regulation (enhancement or repression of transcription) of 285 was examined by the mammalian One-Hybrid System. As a result, 285 was revealed to repress the transcriptional activity of the CMV promoter. Thus, the function of the 285 as a transcription factor was revealed.

The present invention was accomplished based on the knowledge described above, which provides novel proteins "285" having zinc finger domains that bind to a GC-box, genes encoding the proteins, and molecules functionally equivalent thereto, as well as production and use thereof.

More specifically, the present invention provides:

(1) a DNA selected from the group consisting of:
(a) a DNA encoding a protein comprising the amino acid sequence of SEQ ID NO: 2 or 4;
(b) a DNA comprising the coding region of the nucleotide sequence of SEQ ID NO: 1 or 3;
(c) a DNA encoding a protein comprising the amino acid sequence of SEQ ID NO: 2 or 4 in which one or more amino acids are substituted, deleted, inserted, and/or added, and wherein the protein is functionally equivalent to the protein consisting of the amino acid sequence of SEQ ID NO: 2 or 4; and
(d) a DNA hybridizing under stringent conditions with a DNA consisting of the nucleotide sequence of SEQ ID NO: 1 or 3 which encodes a protein functionally equivalent to the protein consisting of the amino acid sequence of SEQ ID NO: 2 or 4;
(2) a DNA encoding a partial peptide of the protein consisting of the amino acid sequence of SEQ ID NO: 2 or 4;
(3) a protein or a peptide encoded by the DNA of (1) or (2);
(4) a vector into which the DNA of (1) or (2) is inserted;
(5) a transformed cell retaining the DNA of (1) or (2), or the vector of (4);
(6) a method for producing the protein or peptide of (3), wherein the method comprises the steps of: culturing the host cell of (5), and recovering the expressed protein from said host cell or the culture supernatant thereof;
(7) an antibody binding to the protein of (3);
(8) a polynucleotide comprising at least 15 nucleotides which is complementary to either a DNA consisting of the nucleotide sequence of SEQ ID NO: 1 or 3, or the complementary strand thereof;
(9) a method of screening for a compound that binds to the protein of (3), wherein the method comprises the steps of:
(a) contacting said protein or partial peptide thereof with a test sample;
(b) detecting the binding activity of said protein or partial peptide thereof with the test sample; and
(c) selecting the compound that binds to said protein or partial peptide thereof;
(10) a method of screening for a compound that controls the transcriptional regulation activity of the protein of (3), wherein the method comprises the steps of:
(a) contacting said protein or partial peptide thereof with a test sample;
(b) detecting the transcriptional regulation activity of said protein or partial peptide thereof; and
(c) selecting the compound that decreases or increases the transcriptional regulation activity detected in (b) compared with that observed in the absence of the test sample;
(11) a compound that can be isolated by the screening method of (9) or (10);
(12) a promoter activity regulator comprising the protein or peptide of (3), or a DNA encoding them; and
(13) a promoter activity regulator of (12) wherein the promoter is the CMV promoter.

The present invention provides a murine derived gene "m285" and human derived gene "h285", which encode novel proteins with zinc finger domains that bind to a GC-box; hereinafter, "m285" and "h285" are collectively designated as "285" if necessary.

The nucleotide sequences of m285 and h285 are shown in SEQ ID NO: 1 and 3, respectively. The amino acid sequences of the proteins encoded by m285 and h285 are shown in SEQ ID NO: 2 and 4, respectively.

m285 gene of the present invention was isolated as a novel gene whose expression increases shortly after the induction of differentiation by adding DMSO to undifferentiated mouse CL6 cells. On the other hand, the h285 gene of the present invention was isolated as a homologue of the m285 of human. According to the result of homology analysis, the proteins encoded by the genes of the present invention comprise three zinc finger domains, which showed high homology with those of the Sp family transcription factors. Further, the proteins were considered to function as a transcription factor due to its distribution in the cell nucleus, and binding by recognizing the nucleotide sequence of a GC-box. Actually, the 285 proteins of the present invention have the function of repressing the CMV promoter activity in MG63 cells. Considering its expression and structural property, the 285 proteins of the present invention were expected to be molecules with an important function in vivo, and thus, serve as practical targets for the development of therapeutic agents. Moreover, the 285 proteins of the present invention, partial peptides thereof, and DNAs encoding them, may be utilized as a drug (reagent and therapeutic agent) that represses the activity of a promoter, such as the CMV promoter.

The present invention includes proteins functionally equivalent to the 285 proteins (proteins consisting of the amino acid sequences of SEQ ID NO: 2 or 4). Such proteins include, for example, mutants and homologues of the 285 proteins. Herein, the term "functionally equivalent" indicates that the protein of interest, identical with the 285 proteins, functions as a transcription factor with zinc finger domain(s). Specifically, such functions include, for example, binding to a GC-box through zinc finger domain(s), repression of the CMV promoter activity in MG63 cells, and so on.

A binding activity of a protein of interest to a GC-box can be determined, for example, by the gel shift assay as described in Examples. Specifically, after mixing an objective protein and labeled DNA probes comprising a GC-box, non-denaturing polyacrylamide gel electrophoresis is carried out to detect the mobility of the labeled DNA probes on the gel. When the objective protein binds to the labeled DNA comprising a GC-box, the mobility of the band of the DNA-protein complex is lower than that of the labeled DNA alone. Therefore, by detecting a band with low mobility, the objective protein can be judged to bind to a GC-box. Alternatively, repression of the CMV promoter activity in MG63 cells by an objective protein can be determined by repression assay described in Example 8.

As a method well known to those skilled in the art for preparing a protein functionally equivalent to a given protein, methods for introducing mutations into proteins are known. For example, one skilled in the art can prepare proteins functionally equivalent to the 285 proteins by introducing an appropriate mutation in the amino acid sequence of the proteins by site-directed mutagenesis (Hashimoto-Gotoh T. et al. (1995) Gene 152, 271-275; Zoller M J. and Smith M. (1983) Methods Enzymol. 100, 468-500; Kramer W. et al. (1984) Nucleic Acids Res. 12, 9441-9456;Kramer W. and Fritz H J.(1987) Methods. Enzymol. 154, 350-367; Kunkel T A. (1985) Proc. Natl. Acad. Sci. USA. 82, 488-492; Kunkel (1988) Methods Enzymol. 85, 2763-2766). Mutation of amino acids can occur in nature too. The proteins of the present invention include those proteins that comprise the amino acid sequences of the 285 proteins, wherein one or more amino acids are mutated, yet are functionally equivalent to the proteins comprising the sequence of 285 proteins. It is considered that the number of amino acids to be mutated in such a mutant is generally 50 amino acids or less, preferably 30 amino acids or less, more preferably 10 amino acids or less (for example, 5 amino acids or less).

As for the amino acid residue to be mutated, it is preferable that it is mutated into a different amino acid so that the properties of the amino acid side-chain are conserved. Examples of properties of amino acid side chains are hydrophobic amino acids (A, I, L, M, F, P, W, Y, V), hydrophilic amino acids (R, D, N, C, E, Q, G, H, K, S, T), and amino acids comprising the following side chains: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W) (The parenthetic letters indicate the one-letter codes for amino acids).

It is well known that a protein having deletion, addition, and/or substitution of one or more amino acid residues in its sequence can retain the original biological activity (Mark D F. et al. (1984) Proc. Natl. Acad. Sci. U.S.A. 81, 5662-5666; Zoller M J. and Smith M. (1982) Nucleic Acids Res. 10, 6487-6500;Wang A. et al. Science 224,1431-1433; Dalbadie-McFarland G. et al. (1982) Proc. Natl. Acad. Sci. U.S.A. 79, 6409-6413).

A fusion protein comprising a 285 protein is encompassed in the protein, wherein plural amino acid residues are added to the amino acid sequence of 285 proteins. Fusion proteins are fusions of these proteins with other peptides or proteins, and are included within the scope of the present invention. Fusion proteins can be made by techniques well known to a person skilled in the art, such as, by linking the DNA encoding a 285 protein with DNA encoding other peptides or proteins so that the frames match, inserting this linked-DNA into an expression vector, and expressing it in a host. There is no restriction as to what peptides or proteins may be fused to a protein of the present invention.

Known peptides, for example, FLAG (Hopp, T. P. et al., Biotechnology (1988) 6, 1204-1210), 6×His consisting of six His (histidine) residues, 10×His, Influenzaagglutinin (HA), humanc-myc fragment, VSV-GP fragment, p18HIV fragment, T7-tag, HSV-tag, E-tag, SV40T antigen fragment, lck tag, α-tubulin fragment, B-tag, Protein C fragments, etc. can be used as peptides to be fused to a protein of the present invention. Examples of proteins that may be fused to a protein of the present invention include, but are not limited to, GST (glutathione-S-transferase), Influenza agglutinin (HA), immunoglobulin constant region, β-galactosidase, MBP (maltose-binding protein), etc. Fusion proteins can be prepared by fusing commercially available DNA encoding these peptides or proteins with a DNA encoding a protein of the present invention, and expressing the fused DNA thus prepared.

In addition, as a method that is well known to those skilled in the art for preparing proteins that are functionally equivalent to a known protein, hybridization techniques can be employed (Sambrook J. et al. (1989) Molecular Cloning 2nd ed., 9.47-9.58, Cold Spring Harbor Lab. press). More specifically, those skilled in the art may readily isolate DNAs having high homology to the DNA sequences (SEQ ID NO: 1 or 3) encoding the 285 proteins, based on the entire DNA sequence or parts thereof, and isolate DNA-encoding proteins functionally equivalent to the 285 proteins from these DNAs.

The present invention includes proteins that are functionally equivalent to a 285 protein, and which are encoded by DNAs that hybridizes with a DNA-encoding a 285 protein. Such proteins include, for example, homologues from mice and other mammals (e.g., proteins from human, rats, rabbits, cattle, and so on).

Hybridization conditions for isolating DNAs encoding proteins that are functionally equivalent to a 285 protein can be appropriately selected by those skilled in the art. Conditions for hybridization, for example, may be those with low stringency. Low stringency conditions means that the washing conditions after hybridization are, for example, 42° C., 0.1×SSC, and 0.1% SDS, or preferably 50° C., 0.1×SSC, and 0.1% SDS. Examples of hybridization conditions that are more preferable are conditions with high stringency. An example of high stringency conditions is 65° C., 5×SSC and 0.1% SDS. Under these conditions, the higher the temperature, the higher the homology of the obtained DNA. However, several factors such as temperature and salt concentration can influence the stringency of hybridization and one skilled in the art can appropriately select these factors to achieve a similar stringency.

However, instead of hybridization, DNA encoding functionally equivalent proteins to a 285 protein can be isolated via gene amplification methods like polymerase chain reaction (PCR), which uses primers that are synthesized based on the sequence information of a DNA encoding a 285 protein (SEQ ID NO: 1 or 3).

A protein that is functionally equivalent to a 285 protein, encoded by a DNA that is isolated by such hybridization techniques and gene amplification techniques, will normally have a high amino acid sequence homology to a 285 protein (SEQ ID NO: 2 or 4). The proteins of this invention also include proteins that are functionally equivalent to a 285 protein in addition to having a high sequence homology to the amino acid sequence of the 285 protein. High sequence homology of a protein typically means that in its amino acids, usually a homology of at least 50% or more is present, preferably a homology of 75% or more, more preferably a homology of 85% or more, and most preferably a homology of 95% or more. In order to determine the homology of a protein, an algorithm that is described in the literature can be used (Wilbur W J. and Lipman D J. (1983) Proc. Natl. Acad. Sci. USA 80, 726-730).

The proteins of this invention may have different amino acid sequences, molecular weights, and isoelectric points. They may also have differences in the presence or absence of sugar chains and their forms, depending on the cells or hosts that produce these proteins or the production method (described later). However, so long as the obtained protein has the same function as a 285 protein, it is within the scope in the present invention. For example, if a protein of this invention is expressed in a prokaryotic cell such as E. coli a methionine residue will be added to the N terminus of the amino acid sequence of the original protein. The proteins of this invention will also include such proteins.

The proteins of the present invention can be prepared as recombinant proteins or naturally occurring proteins, via methods well known by those skilled in the art. A recombinant DNA can be prepared by inserting a DNA (for example, the DNA comprising the nucleotide sequence of SEQ ID NOs: 1 or 3) which encodes a protein of the present invention into an appropriate vector, collecting the recombinant obtained by introducing the vector into appropriate host cells, obtaining the extract, and purifying by subjecting the extract to chromatography such as ion exchange, reverse, gel filtration, or affinity chromatography in which an antibody against a protein of the present invention is fixed on column or by combining more than one of these columns.

In addition, when a protein of the present invention is expressed in host cells (for example, animal cells and E. coli) as a fusion protein with glutathione-S-transferase protein or as a recombinant protein supplemented with multiple histidines, the expressed recombinant protein can be purified using a glutathione column or a nickel column. After purifying the fusion protein, it is also possible to exclude regions other than the objective protein by cutting with thrombin or factor-Xa, as required.

A naturally occurring protein can be isolated by methods known by a person skilled in the art, for example, using an affinity column in which the antibody binding to a protein of the present invention (described below) is bound against an extract of tissues or cells expressing a protein of the present invention. The antibody can be a polyclonal or a monoclonal antibody.

The present invention also contains partial peptides of the proteins of the present invention. A partial peptide of the present invention comprises at least 7 amino acids or more, preferably 8 amino acids or more, and more preferably 9 amino acids or more. The partial peptides can be used, for example, for preparing an antibody against a protein of the present invention, screening a compound binding to a protein of the present invention, and for screening accelerators or inhibitors of a protein of the present invention. The partial peptides can also be used as antagonists or competitive inhibitors against a protein of the present invention. Because the 285 proteins of the present invention have a GC-box binding activity, nuclear localization activity and transcription regulating activity, partial peptides of this invention include partial peptides having at least one activity among these activities. A partial peptide of the invention can be produced by genetic engineering, known methods of peptide synthesis, or by digesting a protein of the invention with an appropriate peptidase. For peptide synthesis, for example, solid phase synthesis or liquid phase synthesis may be employed.

A DNA encoding a protein of the present invention can be used for the production of the protein in vivo or in vitro as described above. A DNA encoding a protein of the present invention can also be used for application to gene therapy for diseases attributed to genetic abnormality in the gene encoding a protein of the present invention. Any form of the DNA can be used, as long as it encodes a protein of the present invention. Specifically, cDNA synthesized from mRNA, genomic DNA, or chemically synthesized DNA can be used. The present invention includes a DNA comprising a given nucleotide sequence based on degeneracy of genetic codons, as long as it encodes a protein of the present invention.

A DNA of the present invention can be prepared by methods known to those skilled in the art. For example, a DNA of the present invention can be prepared from a cDNA library from cells which express a protein of the present invention by conducting hybridization using a partial sequence of a DNA of the present invention (e.g., SEQ ID NO: 1 or 3) as a probe. A cDNA library can be prepared, for example, by the method described by Sambrook J. et al. (Sambrook J. et al. (1989) Molecular Cloning, Cold Spring Harbor Laboratory Press), or by using commercially available cDNA libraries. A cDNA library can be also prepared by extracting RNA from cells expressing a protein of the present invention, synthesizing cDNA using reverse transcriptase, synthesizing an oligo DNA base on the sequence of the DNA of the present invention (for example, SEQ ID NOs: 1 or 3), conducting PCR using these as primers, and amplifying cDNA encoding the protein of the present invention.

In addition, by sequencing the nucleotides of the obtained cDNA, a translation region encoded by the cDNA can be determined, and the amino acid sequence of a protein of the present invention can be obtained. Moreover, by screening the genomic DNA library using the obtained cDNA as a probe genomic DNA can be isolated.

More specifically, mRNAs may first be prepared from a cell, tissue, or organ (for example, testis, brain, heart, liver, and kidney) in which a protein of the invention is expressed. Known methods can be used to isolate mRNAs. For instance, total RNA is prepared by the guanidine ultracentrifugation method (Chirgwin J M. et al. (1979) Biochemistry 18, 5294-5299) or by the AGPC method (Chomczynski P. and Sacchi N. (1987) Anal. Biochem. 162, 156-159), and mRNA is purified from total RNA using mRNA Purification Kit (Pharmacia). Alternatively, mRNA may be directly purified by the QuickPrep mRNA Purification Kit (Pharmacia).

The obtained mRNA is used to synthesize cDNA using reverse transcriptase. A cDNA may be synthesized using kits, such as the AMV Reverse Transcriptase First-strand cDNA Synthesis Kit (Seikagaku Kogyo). Alternatively, a cDNA may be synthesized and amplified according to the 5'-RACE method (Frohman M A. et al. (1988) Proc. Natl. Acad. Sci. U.S.A. 85, 8998-9002; Belyavsky A. et al. (1989) Nucleic Acids Res. 17:2919-2932) wherein primers, described herein, the 5'-Ampli FINDER RACE Kit (Clontech), and polymerase chain reaction (PCR) are used.

A desired DNA fragment is prepared from the PCR products and ligated with a vector DNA. The recombinant vectors are used to transform E. coli and a desired recombinant vector is prepared from a selected colony. The nucleotide sequence of the desired DNA can be verified by conventional methods, such as, the dideoxynucleotide chain termination method.

A DNA of the invention may be also designed to have a sequence that is expressed more efficiently by taking into account the frequency of codon usage in the host to be used for expression (Grantham R. et al. (1981) Nucleic Acids Res. 9, 43-74). A DNA of the present invention may be altered by a commercially available kit or a conventional method. For instance, a DNA may be altered by digestion with restriction enzymes, insertion of synthetic oligonucleotides or appropriate DNA fragments, addition of linkers, or insertion of the initiation codon (ATG) and/or the stop codon (TAA, TGA, or TAG) The DNAs of the present invention specifically encompass a DNA consisting of the nucleotide sequence from the 75$^{th}$ nucleotide Adenine to the 1271$^{st}$ nucleotide Adenine of SEQ ID NO: 1, and a DNA comprising this nucleotide sequence. Further, a DNA consisting of the nucleotide sequence from the 1$^{st}$ nucleotideAdenine to the 1197$^{th}$ nucleotide Adenine of SEQ ID NO: 3, and a DNA comprising this nucleotide sequence are also encompassed by the DNAs of the present invention.

The DNAs of this invention include a DNA that (a) hybridizes with a DNA consisting of the nucleotide sequence of SEQ ID NO: 1 or 3; and (b) encodes a protein that is functionally equivalent to a protein of this invention mentioned above. Conditions for hybridization can be selected appropriately by those skilled in the art, and those conditions specifically mentioned above may be used. Under these conditions, DNA having higher homology is obtained as the temperature is raised. The above-mentioned DNA to be hybridized is preferably a naturally occurring DNA, for example, a cDNA or chromosomal DNA.

The present invention also provides vectors into which a DNA of the present invention is inserted. The vectors of the present invention are useful to retain a DNA of the present invention in host cell, or to express a protein of the present invention.

When *E. coli* is used as the host cell and a vector is amplified therein to produce a large amount in *E. coli* (e.g., JM109, DH5α, HB101, or XL1Blue), the vector should have an "ori" that may be amplified in *E. coli* and a marker gene (e.g., ampicillin, tetracycline, kanamycin, or chloramphenicol)) that enables selection of transformed *E. coli* (e.g., a drug-resistance gene selected by a drug. For example, the M13-series vectors, the pUC-series vectors, pBR322, pBluescript, pCR-Script, etc. can be used. In addition to the vectors described above, pGEM-T, pDIRECT, and pT7 can also be used for subcloning and extracting cDNA. When a vector is used to produce a protein of the present invention, an expression vector is especially useful. For example, an expression vector to be expressed in *E. coli* should have the above characteristics to be amplified in *E. coli*. When *E. coli* (e.g., JM109, DH5α, HB101 or XL1 Blue) are used as the host cell, in addition to the above characteristics, the vector should have a promoter like the lacz promoter (Ward et al. (1989) Nature 341, 544-546; (1992) FASEB J. 6, 2422-2427), the araB promoter (Better et al. (1988) Science 240, 1041-1043), or the T7 promoter that can efficiently express the desired gene in *E. coli*. As such a vector, for example, pGFX-5X-1 (Pharmacia), "QIAexpress system" (Qiagen), pEGFP or pET (in this case, the host is preferably BL21 which expresses T7 RNA polymerase) can be used in addition to the above vectors.

A vector also may contain a signal sequence for polypeptide secretion. As a signal sequence for protein secretion, the pelB signal sequence (Lei S P. et al. (1987) J. Bacteriol. 169, 4379) can be used in the case of producing proteins into the periplasm of *E. coli*. For introducing a vector into host cells, for example, the calcium chloride method and the electroporation method can be used.

Besides *E. coli*, expression vectors derived from mammals (for example, pcDNA3 (Invitrogen) and pEGF-BOS (Nucleic Acids. Res. 1990, 18 (17), p5322), pEF, pCDM8); expression vectors derived from insect cells (for example, "Bac-to-BAC baculovirus expression system" (GIBCO BRL), pBacPAK8); expression vectors derived from plants (for example pMH1, pMH2); expression vectors derived from animal viruses (for example, pHSV, pMV, pAdexLcw); expression vectors derived from retroviruses (for example, pZIPneo); expression vectors derived from yeast (for example, "Pichia Expression Kit" (Invitrogen), pNV11, SP-Q01); expression vectors derived from *Bacillus subtilis* (for example, pPL608, pKTH50) can be used as vectors for producing a protein of the present invention.

In order to express a vector in animal cells, such as CHO, COS, or NIH3T3 cells, the vector should have a promoter necessary for expression in such cells, for example, the SV40 promoter (Mulligan et al. (1979) Nature 277, 108), the MMLV-LTR promoter, the EF1α promotor (Mizushima et al. (1990) Nucleic Acids Res. 18, 5322), or the CMV promoter, etc. and preferably a marker gene for selecting transformants (for example, a drug resistance gene selected by a drug (e.g., neomycin, G418)). Examples of vectors with these characteristics include, but are not limited to, pMAM, pDR2, pBK-RSV, pBK-CMV, pOPRSV, pOp13, and so on.

In addition, methods to stably express a gene and amplifying the copy number of the gene in cells include: for example, a method wherein a vector comprising the complementary DHFR gene (for example pCHO I) is introduced into CHO cells with deleted nucleic acid synthesizing pathway, and the vector is amplified by the addition of methotrexate (MTX). On the other hand, in the case of transient expression of a gene, a method wherein a vector (e.g., pcD) comprising replication origin of SV40 is transformed using COS cells comprising the SV40 T antigen expressing gene on chromosomes can be used. The origin used for replication may be those of polyomavirus, adenovirus, bovine papilloma virus (BPV), etc. In addition, the expression vector may include a selection marker gene for amplification of the gene copies in host cells. Examples of such markers include, but are not limited to, the aminoglycoside transferase (APH) gene, the thymidine kinase (TK) gene, the *E. coli* xanthine-guanine phosphoribosyl transferase (Ecogpt) gene, and the dihydrofolate reductase (dhfr) gene.

On the other hand, a gene of the present invention can be expressed in vivo in animals, for example, by inserting a DNA of the present invention into an appropriate vector and introducing the vector in vivo by conventional methods, such as the retrovirus method, the liposome method, the cationic liposome method, and the adenovirus method. According to such methods, gene therapy against diseases attributed to mutation of the h285 gene of the present invention can be affected. As a vector, for example, adenovirus vector (for example pAdexlcw), and retrovirus vector (for example, pZIPneo) can be used; however, the present invention is not restricted thereto. Common gene manipulation, for example, insertion of a DNA of the present invention into a vector, can be performed according to any standard method (Molecular Cloning, 5.61-5.63) Administration into a living body can be either an ex vivo method, or in vivo method.

The present invention provides a transformed cell that retains a DNA or vector of the present invention. The host cell into which a vector of the invention is introduced is not particularly limited. *E. coli* or various animal cells can be used. The transformed cells of the present invention can be used as a production system for producing or expressing a protein of the present invention. The present invention provides methods of producing a protein of the invention either in vitro or in vivo. For in vitro production, eukaryotic cells or prokaryotic cells can be used as host cells.

Useful eukaryotic cells as host include animal, plant, or fungi cells. The following can be used: animal cells/mammalian cells, such as CHO (J. Exp. Med. 108, 945 (1995)), COS, 3T3, myeloma, baby hamster kidney (BHK), HeLa, and Vero cells; amphibian cells, such as Xenopus oocytes (Valle et al. (1981) Nature 291,340-358); or insect cells, such as Sf9, Sf21, and Tn5 cells. CHO cells lacking the DHFR gene (dhfr-CHO) (Proc. Natl. Acad. Sci. U.S.A. 77, 4216-4220 (1980)) or CHO K-1 (Proc. Natl. Acad. Sci. U.S.A. 60, 1275 (1968)) may also be used. In animal cells, CHO cells are particularly preferable for mass expression. A vector can be introduced into host cells by, for example via the calcium phosphate method, the DEAE dextran method, the cationic liposome DOTAP (Boehringer Mannheim), the electroporation method, or the lipofection method.

Plant cells originating from *Nicotiana tabacum* are a known protein-production system and may be used as callus cultures. Fungi cells, yeast cells such as *Saccharomyces* (including *Saccharomyces cerevisiae*) or filamentous fungi, such as, *Aspergillus* (including *Aspergillus niger*) are known and may be used herein.

Useful prokaryotic cells include bacterial cells, such as, *E. coli*, for example, JM109, DH5α, HB101 are known. Regarding others, *Bacillus subtilis* is known.

These host cells are transformed by a desired DNA, and the resulting transformants are cultured in vitro to obtain a protein. Transformants can be cultured using known methods. Culture medium for animal cell, for example, DMEM, MEM, RPMI1640, or IMDM may be used with or without serum supplement such as fetal calf serum (FCS). The pH of the culture medium is preferably between about pH 6 to 8. Such cells are typically cultured at about 30 to 40° C. for about 15 to 200 hr, and the culture medium may be replaced, aerated, or stirred if necessary.

Animal and plant hosts may be used for in vivo production. For example, a desired DNA can be introduced into an animal or plant host. Encoded proteins are produced in vivo, and then recovered. These animal and plant hosts are included in the host cells of the present invention.

Animals to be used for the production systems described above include, but are not limited to, mammals and insects. Mammals, such as, goat, porcine, sheep, mouse and bovine may be used (Vicki Glaser (1993) SPECTRUM Biotechnology Applications). Alternatively, the mammals may be transgenic animals.

For instance, a desired DNA may be prepared as a fusion gene with a gene encoding a protein specifically produced in milk, such as goat β casein. DNA fragments comprising a fusion gene having the desired DNA are injected into goat embryos, which are then introduced back to female goats. Proteins are recovered from milk produced by the transgenic goats (i.e., those born from the goats that had received the modified embryos) or from their offspring. To increase the amount of milk containing the proteins produced by transgenic goats, appropriate hormones may be administered to them (Ebert K M. et al. (1994) Bio/Technology 12, 699-702).

Alternatively, insects like the silkworm may be used. A desired DNA inserted into baculovirus can be used to infect silkworms, and a desired protein is then recovered from their body fluid (Susumu M. et al. (1985) Nature 315, 592-594).

As plants, tobacco can be used. In use of tobacco, a desired DNA is inserted into a plant expression vector, such as pMON530, which is then introduced into bacteria, such as *Agrobacterium tumefaciens*. Then, the bacteria are used to infect tobacco like *Nicotiana tabacum*, and a desired polypeptide is recovered from the leaves of the plant (Julian K. -C. Ma et al. (1994) Eur. J. Immunol. 24, 131-138).

A protein of the present invention obtained as above may be isolated from the interior or exterior (e.g., medium) of the cells or hosts, and purified as a substantially pure homogeneous protein. The method for protein isolation and purification is not limited to any specific method. In fact, any standard method may be used. For instance, column chromatography, filtration, ultrafiltration, salt precipitation, solvent precipitation, solvent extraction, distillation, immunoprecipitation, SDS-polyacrylamide gel electrophoresis, isoelectric point electrophoresis, dialysis, and recrystallization may be appropriately selected and combined to isolate and purify the protein.

For chromatography, for example, affinity chromatography, ion-exchange chromatography, hydrophobic chromatography, gel filtration, reverse phase chromatography, adsorption chromatography, and such may be used (ed. Daniel R. Marshak et al. (1996) Strategies for Protein Purification and Characterization: A Laboratory Course Manual., Cold Spring Harbor Laboratory Press). These chromatographies may be performed by liquid chromatography, such as, HPLC and FPLC. Thus, the present invention provides highly purified proteins produced by the above methods.

A protein of the present invention may be optionally modified or partially deleted by treating it with an appropriate protein-modification enzyme before or after purification. Useful protein-modification enzymes include, but are not limited to, trypsin, chymotrypsin, lysylendopeptidase, protein kinase, and glucosidase.

The present invention provides antibodies that bind to a protein of the invention. An antibody of the invention can be used in any form, such as monoclonal or polyclonal antibodies, and includes antiserum obtained by immunizing a rabbit with a protein of the invention, all classes of polyclonal and monoclonal antibodies, human antibodies, and humanized antibodies produced via genetic recombination.

A protein of the invention used as an antigen to obtain an antibody may be derived from any animal species, but is preferably derived from a mammal such as a human, mouse, or rat, more preferably from a human. A human-derived protein may be obtained from the nucleotide or amino acid sequences disclosed herein.

In the present invention, a protein to be used as an immunization antigen may be a complete protein or a partial peptide of a protein. A partial peptide may be, for example, an amino (N)-terminal or carboxy (C)-terminal fragment of the protein. Herein, "an antibody" is defined as an antibody that specifically reacts with either the full-length or a fragment of a protein.

A gene encoding a protein of the invention or its fragment may be inserted into a known expression vector, which is then used to transform a host cell as described herein. The desired protein or its fragment may be recovered from the exterior or interior of the host cells by any standard method, and may be used as an antigen. Alternatively, cells expressing the protein or their lysates, or a chemically synthesized protein may be used as an antigen. Short peptides are preferably bound with carrier proteins such as bovine serum albumin, ovalbumin, and keyhole limpet hemocyanin to be used as the antigen.

Any mammalian animal may be immunized with the antigen, but preferably the compatibility with parental cells used for cell fusion is taken into account.

In general, animals of the orders Rodentia, Lagomorpha, or Primate are used. Animals of Rodentia, rodents, include, for example, mouse, rat, and hamster. Animals of Lagomorpha, lagomorphs, include, for example, rabbit. Animals of Primate, primates, include, for example, a monkey of catarrhine (old world monkey) such as *Macaca fascicularis*, rhesus monkey, sacred baboon, or chimpanzee.

Methods for immunizing animals against antigens are known in the art. Intraperitoneal injection or subcutaneous injection of antigens is used as a standard method for immunization of mammals. More specifically, antigens may be diluted and suspended in an appropriate amount with phosphate buffered saline (PBS), physiological saline, etc. If desired, the antigen suspension may be mixed with an appropriate amount of a standard adjuvant, such as Freund's complete adjuvant, made into emulsion, and then administered to the mammalian animals. Preferably, it is followed by several administrations of antigen mixed with an appropriately amount of Freund's incomplete adjuvant every 4 to 21 days. An appropriate carrier may also be used for immunization. After immunization as above, serum is examined for increase of the amount of desired antibodies by a standard method.

Polyclonal antibodies against a protein of the present invention may be prepared by collecting blood from the immunized mammal examined for the increase of desired antibodies in the serum, and separating serum from the blood by any conventional method. Polyclonal antibodies may be used as serum containing the polyclonal antibodies, or if necessary, a fraction containing the polyclonal antibodies may be isolated from the serum. Immunoglobulin G or M can be prepared by obtaining a fraction which recognizes only a protein of the present invention using an affinity column coupled with the protein of the present invention and further purifying this fraction using protein A or protein G column.

To prepare monoclonal antibodies, immune cells are collected from the mammal immunized against an antigen and checked for the increased level of desired antibodies in the serum as described above, and are subjected to cell fusion. It is preferred that the immune cells used for cell fusion be obtained from spleen. Other parental cells can be fused with the above immunocyte. For example, preferably myeloma cells of mammalians and more preferably myeloma cells that acquired the property for selecting fused cells by drugs, can be used.

The above immunocyte and myeloma cells can be fused by known methods, for example, the method by Milstein et al. (Galfre G. and Milstein C. (1981) Methods Enzymol. 73, 3-46).

Resulting hybridomas obtained by the cell fusion may be selected by cultivating them in a standard selection medium, such as the HAT medium (medium containing hypoxanthine, aminopterin, and thymidine) The cell culture is typically continued in the HAT medium for several days to several weeks, a sufficient time to allow all the other cells, except desired hybridoma (non-fused cells), to die. Then, by the standard limiting dilution method, a hybridoma cell producing the desired antibody is screened and cloned.

In addition to the above method, in which a non human animal is immunized against an antigen for preparing hybridoma, human lymphocytes, such as that infected by EB virus, may be immunized with a protein, protein expressing cells, or their lysates in vitro. Then, the immunized lymphocytes are fused with human-derived myeloma cells capable of indefinitely dividing, such as U266, to yield a hybridoma producing a desired human antibody having binding ability to the protein (Unexamined Published Japanese Patent Application (JP-A) No. Sho 63-17688).

Next, the monoclonal antibody, obtained by transplanting the obtained hybridomas into the abdominal cavity of a mouse and by extracting ascites, can be purified by, for example, ammonium sulfate precipitation, protein A or protein G column, DEAE ion exchange chromatography, or an affinity column to which a protein of the present invention is coupled. An antibody of the present invention can be used for not only purification and detection of a protein of the present invention, but also as a candidate for agonists and antagonists of a protein of the present invention. In addition, an antibody can be applied to antibody treatment for diseases associated with a protein of the present invention. When the obtained antibody is used for the administration to the human body (antibody treatment), a human antibody or a humanized antibody is preferable for reducing immunogenicity.

For example, transgenic animals having a repertory of human antibody genes may be immunized against a protein, protein expressing cells, or their lysates as an antigen. Antibody producing cells are collected from the animals and fused with myeloma cells to obtain hybridomas, from which human antibodies against a protein can be prepared (see WO92-03918, WO93-2227, WO94-02602, WO94-25585, WO96-33735, and WO96-34096).

Alternatively, an immune cell, such as an immunized lymphocyte, producing antibodies may be immortalized by an oncogene and used for preparing monoclonal antibodies.

Monoclonal antibodies thus obtained can be also recombinantly prepared using genetic engineering techniques (see, Borrebaeck C A K. and Larrick J W. (1990) THERAPEUTIC MONOCLONAL ANTIBODIES, published in the United Kingdom by MACMILLAN PUBLISHERS LTD). A DNA encoding an antibody may be cloned from an immune cell, such as a hybridoma or an immunized lymphocyte producing the antibody, inserted into an appropriate vector, and introduced into host cells to prepare a recombinant antibody. The present invention also provides recombinant antibodies prepared as described above.

Furthermore, an antibody of the present invention may be a fragment of an antibody or modified antibody, as long as it binds to one or more of the proteins of the present invention. For instance, the antibody fragment may be Fab, $F(ab')_2$, Fv, or single chain Fv (scFv) in which Fv fragments from H and L chains are ligated by an appropriate linker (Huston J S. et al. (1988) Proc. Natl. Acad. Sci. U.S.A. 85, 5879-5883). More specifically, an antibody fragment may be generated by treating an antibody with enzymes like papain or pepsin. Alternatively, a gene encoding an antibody fragment may be constructed, inserted into an expression vector, and expressed in an appropriate host cell (see, for example, Co MS. et al. (1994) J. Immunol. 152, 2968-2976; Better M. and Horwitz A H. (1989) Methods Enzymol. 178, 476-496; Pluckthun A. and Skerra A. (1989) Methods Enzymol. 178, 497-515; Lamoyi E. (1986) Methods Enzymol. 121, 652-663; Rousseaux J. et al. (1986) Methods Enzymol. 121, 663-669; Bird RE. and Walker BW. (1991) Trends Biotechnol. 9, 132-137).

An antibody may be modified by conjugation with a variety of molecules, such as polyethylene glycol (PEG). The present invention provides such modified antibodies. The modified antibody can be obtained by chemically modifying an antibody. These modification methods are conventional in this field.

Alternatively, an antibody of the present invention may be obtained as a chimeric antibody, where a variable region is derived from nonhuman antibody and the constant region is derived from human antibody; or as a humanized antibody comprising the complementarity determining region (CDR) derived from nonhuman antibody, the frame work region (FR) derived from human antibody, and the constant region.

Obtained antibodies may be purified into homogeneity. An antibody used in the present invention can be separated and purified by conventional methods used for separating and purifying proteins. For example, the separation and purification of a protein can be performed by an appropriately selected and combined use of column chromatography (such as affinity chromatography), filter, ultrafiltration, salting-out, dialysis, SDS polyacrylamide gel electrophoresis, isoelectric focusing, etc. (Antibodies: A Laboratory Manual. Ed Harlow and David Lane, Cold Spring Harbor Laboratory, 1988). However, the present invention is not limited to the above-mentioned techniques. The concentration of antibodies obtained above can be determined by measuring absorbance, by the enzyme-linked immunosorbent assay (ELISA), etc.

Examples of columns used for affinity chromatography include protein A columns and protein G columns. Examples of columns using protein A column include Hyper D, POROS, Sepharose F. F. (Pharmacia) etc.

In addition to affinity chromatography, the chromatography includes, for example, ion-exchange chromatography, hydrophobic chromatography, gel filtration, reverse-phase chromatography, adsorption chromatography, etc. (Strategies for Protein Purification and Characterization: A Laboratory Course Manual. Ed Daniel R. Marshak et al., Cold Spring Harbor Laboratory Press, 1996). The chromatographic procedures can be carried out by liquid-phase chromatography such as HPLC, FPLC, or the like.

For example, measurement of absorbance, enzyme-linked immunosorbent assay (ELISA), enzyme immunoassay (EIA), radioimmunoassay (RIA), and/or immunofluorescence may be used to measure the antigen binding activity of an antibody of the invention. In ELISA, an antibody of the present invention is immobilized on a plate, a protein of the invention is applied to the plate, and then a sample containing a desired antibody, such as culture supernatant of antibody producing cells or purified antibodies, is applied. Then, a secondary antibody that recognizes the primary antibody and is labeled with an enzyme, such as alkaline phosphatase, is applied, and the plate is incubated. Next, after washing, an enzyme substrate, such as p-nitrophenyl phosphate, is added to the plate, and the absorbance is measured to evaluate the antigen binding activity of the sample. A fragment of a protein, such as a C-terminal fragment, may be used as a protein. BIAcore (Pharmacia) may be used to evaluate the activity of an antibody according to the present invention.

The above methods allow for the detection or measurement of the proteins of the invention, by exposing an antibody of the invention to a sample assumed to contain a protein of the invention, and detecting or measuring the immune complex formed by the antibody and the protein. Because the method of detection or measurement of proteins according to the invention can specifically detect or measure proteins, the method may be useful in a variety of experiments in which the protein is used.

The present invention provides a polynucleotide having at least 15 nucleotides that is complementary to a DNA that encodes a 285 protein (SEQ ID NO: 1 or 3) or the complementary strand thereof.

The term "complementary strand," as employed herein, is defined as one strand of a double strand DNA composed of A:T (in the case of RNA, A:U) and G:C base pairs to the other strand. In addition, "complementary" is defined as not only those completely matching within a continuous region of at least 15 nucleotides, but also having a homology of at least 70%, preferably at least 80%, more preferably 90%, and most preferably 95% or higher within that region. The homology may be determined using the algorithm described herein.

Probes or primers for detection and amplification of a DNA encoding a protein of this invention or for detection of an expression of the protein, or nucleotides or nucleotide derivatives for regulating protein expression (for example, antisense oligonucleotides and ribozymes, or DNA encoding them) are included in these polynucleotides. In addition, such polynucleotides may be also used for preparing DNA chips.

When used as a primer, the region on the 3' side is designed to be complementary to a DNA encoding a protein of the invention, and restriction enzyme recognition sequence and tags can be added to the 5' side.

For example, an antisense oligonucleotide that hybridizes with a portion of the nucleotide sequence of SEQ ID NO: 1 or 3 is also included in the antisense oligonucleotides of the present invention. An antisense oligonucleotide is preferably one against at least 15 continuous nucleotides in the nucleotide sequence of SEQ ID NO: 1 or 3. More preferably, it is an antisense oligonucleotide having at least 15 continuous nucleotides that contains the translation initiation codon.

Derivatives or modified products of antisense oligonucleotides can be used as antisense oligonucleotides. Examples of such modified products are, lower alkyl phosphonate modifications such as methyl-phosphonate-type or ethyl-phosphonate-type, phosphothioate modifications and phosphoamidate modifications.

The term "antisense oligonucleotides" as used herein, means not only those in which the entire nucleotides corresponding to those constituting a specified region of a DNA or mRNA are complementary, but also those having a mismatch of one or more nucleotides, so long as the DNA or mRNA and the oligonucleotide can hybridize to each other in a nucleotide sequence (i.e., SEQ ID NO: 1 or 3) specific manner.

An antisense oligonucleotide derivative of the present invention has inhibitory effect on the function of a protein of the present invention as a result that the derivative inhibits the expression of the protein of the invention by acting upon cells producing the protein of the invention and by binding to the DNA or mRNA encoding the protein to inhibit its transcription or translation or to promote the degradation of the mRNA.

An antisense oligonucleotide derivative of the present invention can be made into an external preparation, such as a liniment and a poultice, by mixing with a suitable base material which is inactive against the derivatives.

In addition, as necessary, the derivatives can be formulated into tablets, powders, granules, capsules, liposome capsules, injections, solutions, nose-drops, and freeze-drying agents and such by adding excipients, isotonic agents, solubilizing agents, stabilizers, preservative substance, painkillers, etc. These can be prepared by following usual methods.

An antisense oligonucleotide derivative of the present invention is given to a patient by directly applying onto the ailing site or by injecting into a blood vessel so that it will reach the site of ailment. An antisense-mounting medium can also be used to increase durability and membrane-permeability. Examples are liposome, poly-L-lysine, lipid, cholesterol, lipofectin or derivatives of these.

The dosage of an antisense oligonucleotide derivative of the present invention can be adjusted suitably according to the patient's condition and used in desired amounts. For example, a dose range of 0.1 to 100 mg/kg, preferably 0.1 to 50 mg/kg can be administered.

An antisense oligonucleotide of the invention inhibits the expression of a protein of the invention and thereby is useful for suppressing the biological activity of the protein of the invention. In addition, expression-inhibitors comprising an antisense oligonucleotide of the invention are useful in that they can inhibit the biological activity of a protein of the invention. It is thought that it is possible to use an antisense oligonucleotides of this invention for suppressing biological activities of a protein of the invention.

A protein of the invention may be used for screening compounds binding to the protein. Specifically, a protein may be used in methods of screening for compounds comprising the steps of: (1) contacting a protein of the present invention to a test sample in which a compound binding to the protein is expected to be contained; and (2) selecting the compound having the binding activity to the protein.

A protein of the present invention to be used for screening may be a recombinant protein, a protein derived from the nature, or partial peptide thereof. Alternatively, the protein may be in a form expressed on a cell surface or in a form of cell membrane fraction. Any test sample, for example, cell extracts, cell culture supernatant, products of fermenting microorganism, extracts from marine organism, plant extracts, purified or crude proteins, peptides, non-peptide compounds, synthetic low molecular compounds and naturally-occurring compounds, can be used. A protein of the present invention can be contacted with a test sample in the following forms: as a purified protein, a soluble protein, a form bound to a carrier, a fusion protein with another protein, a form expressed on cell membrane, or a cell membrane fraction.

By using a protein of the present invention, for example, in a method for screening for proteins binding to the protein thereof, many methods well known by a person skilled in the art can be used. Such a screening can be conducted by, for example, the immunoprecipitation method, specifically, in the following manner. A gene encoding a protein of the present invention is expressed in a host cell, such as an animal cell, by inserting the gene into an expression vector for foreign gene, such as pSV2neo, pcDNA I, pCD8. As a promoter to be used for the expression, any promoter which can be generally used can be selected; for example, the SV40 early promoter (Rigby in Williamson (ed.) (1982) Genetic engineering, vol.3. Academic Press, London, p. 83-141), the EF-1α promoter (Kim et al. (1990) Gene 91, 217-223), the CAG promoter (Niwa et al. (1991) Gene 108, 193-200) the RSV LTR promoter (Cullen (1987) Methods in Enzymology 152, 684-704), the SRα promoter (Takebe et al. (1988) Mol. Cell. Boil. 8, 466), the CMV immediate early promoter (Seed and Aruffo (1987) Proc. Natl. Acad. Sci USA 84, 3365-3369), the SV40 late promoter (Gheysen and Fiers (1982) J. Mol. Appl. Genet. 1, 385-394), the Adenovirus late promoter (Kaufman et al. (1989) Mol. Cell. Biol. 9, 946), the HSV TK promoter, and so on may be used.

To express a foreign gene by introducing the gene into animal cells, the electroporation method (Chu G. et al. (1987) Nucl. Acid Res. 15, 1311-1326), the calcium phosphate method (Chen C and Okayama H. (1987) Mol Cell. Biol. 7, 2745-2752), the DEAE dextran method (Lopata M A. et al. (1984) Nucl. Acids Res. 12, 5707-5717; Sussman D J. and Milman G. (1985) Mol. Cell. Biol. 4, 1642-1643), the Lipofectin method (Derijard B. (1994) Cell 7, 1025-1037; Lamb B T. et al. (1993) Nature Genetics 5, 22-30; Rabindran S K. et al. (1993) Science 259, 230-234) etc. can be used.

A protein of the present invention can be expressed as a fusion protein comprising a recognition site (epitope) of a monoclonal antibody by introducing the epitope of the monoclonal antibody, whose property has been revealed, to N or C terminus of the protein of the present invention. A commercially available epitope-antibody system can be used (Experimental medicine 13, 85-90 (1995)). Through a multiple cloning site, a vector which can express a fusion protein with, for example, β-galactosidase, maltose-binding protein, glutathione S-transferase, green florescence protein (GFP), is available in the market.

Methods have been reported in which fusion proteins are prepared by introducing only small epitopes comprising several to a dozen of amino acids, so that the properties of the proteins of the present invention may not change by making the proteins fusion proteins. Epitopes, for example, polyhistidine (His-tag), influenza aggregate HA, human c-myc, FLAG, Vesicular stomatitis virus glycoprotein (VSV-GP), T7 gene 10 protein (T7-tag), human simple herpes virus glycoprotein (HSV-tag), epitope such as E-tag (an epitope on monoclonal phage), and monoclonal antibodies recognizing these can be used as an epitope-antibody system for screening a protein binding to a protein of the present invention (Experimental Medicine 13, 85-90 (1995)).

In the immunoprecipitation, an immune complex is formed by adding these antibodies to cell-eluate prepared using an appropriate detergent. This immune complex comprises a protein of the present invention, a protein having a binding affinity for the protein, and an antibody. Immunoprecipitation can be conducted with an antibody against a protein of the present invention, besides-using antibodies against the above epitopes. An antibody against a protein of the present invention can be prepared, for example, by introducing a gene encoding the protein of the present invention into an appropriate E. coli expression vector; expressing the gene in E. coli; purifying the expressed protein; and immunizing animals, for example, rabbits, mice, rats, goats, domestic fowls, etc. with such protein. The antibody can be prepared also by immunizing the above animals against a synthesized partial peptide of a protein of the present invention.

An immune complex can be precipitated, for example, by Protein A Sepharose or Protein G Sepharose when the antibody is mouse IgG antibody. When a protein of the present invention is prepared as a fusion protein with an epitope, for example GST, an immune complex can be formed by using a substance specifically binding to these epitopes, such as glutathione-Sepharose 4B, in the same manner as in the use of an antibody-against a protein of the present invention.

Popular Immunoprecipation can be performed by following or according to, for example, the reference (Harlow, E. and Lane, D. (1988) Antibodies, Cold Spring Harbor Laboratory publications, New York, pp. 511-552,).

SDS-PAGE is commonly used for analysis of immunoprecipitated proteins and the binding protein can be analyzed depending on the molecular weight of the protein by using gel with an appropriate concentration. In general, because it is difficult to detect a protein binding to a protein of the present invention by a common staining method like Coomassie staining or silver staining, the detection sensitivity for the protein can be improved by culturing in a culture medium containing the radioactive isomer, $^{35}S$-methionineor $^{35}S$-cystein, labeling proteins in the cells, and detecting the proteins. The target protein can be purified from the SDS-polyacrylamide gel and its sequence can be determined directly after the molecular weight of the protein is determined.

Moreover, to isolate proteins that bind to a protein of the present invention by using the protein, for example, West western blotting (Skolnik E Y. et al. (1991) Cell 65, 83-90) may be used. More specifically, it is conducted as follows: (1) constructing a cDNA library using a phage vector (λgt11, ZAP, etc.) from cells, tissues, and organs (for example, testis, brain, heart, liver, and kidney) that are expected to express binding proteins that bind to the protein of this invention; (2) expressing the cDNA library on LB-agarose and immobilizing the expressed protein onto a filter; (3) reacting the purified and labeled protein of this invention with the filter; and (4) detecting the plaque expressing the protein that binds to the protein of this invention by the label. Methods to label a protein of this invention may be a method that utilizes the binding characteristics of biotin and avidin; a method utilizing antibodies that bind specifically to the protein of this invention or to peptides or polypeptides fused to the protein of this invention (for example GST and such); a method that utilizes radioisotopes; a method that utilizes fluorescence; and such.

Further, another embodiment of the screening method of this invention is exemplified by a method utilizing the two-hybrid system using cells (Fields S. and Sternglanz R. (1994) Trends. Genet. 10, 286-292; Dalton S. and Treisman R. (1992) "Characterization of SAP-1, a protein recruited by serum response factor to the c-fos serum response element." Cell 68, 597-612; "MATCHMAKER Two-Hybrid System", "Mammalian MATCHMAKER Two-Hybrid Assay Kit", "MATCHMAKER One-Hybrid System" (all manufactured by Clonetech); and "HybriZAP Two-Hybrid Vector System" (manufactured by Stratagene)). In the two-hybrid system, a protein of this invention or a partial peptide thereof may be fused to the DNA binding region of SRF or GAL4, and expressed in yeast. A cDNA library is constructed from cells predicted to express proteins that bind to the protein of this invention, wherein the cDNA library is constructed in such a way that the proteins are expressed as fusion proteins with transcription activation regions of VP16 or GAL4. The cDNA library is transfected into the above yeast, and then positive clones are detected to isolate the cDNA derived from the library (expression of a protein that binds to the protein of the invention in yeast leads to the binding of the two proteins, and results in the activation of the reporter gene, which allows detecting positive clones) The protein encoded by the isolated cDNA may be obtained by introducing the cDNA into E. coli and expressing it therein. Thus, it is possible to prepare proteins that bind to a protein of this invention and genes encoding them. The reporter gene used in the two-hybrid system may be such as Ade2 gene, Lac Z gene, CAT gene, luciferase gene, PAI-1 (Plasminogen activator inhibitor type 1) gene, and such besides HIS3 gene, but are not limited to these examples. Screening by the two-hybrid method can also be performed using, in addition to yeast, mammalian cells, etc.

A protein binding to a protein of the present invention can be screened using affinity chromatography. For example, a preferred method for screening of the present invention utilizes affinity chromatography. A protein of the invention is immobilized on a carrier of an affinity column, and a test sample, in which a protein capable of binding to the protein of the invention is supposed to be expressed, is applied to the column. A test sample herein may be, for example, cell extracts, cell lysates, etc. After loading the test sample, the column is washed, and proteins bound to the protein of the invention can be prepared.

The amino acid sequence of the obtained protein is analyzed, an oligo DNA is synthesized based on the sequence, and cDNA libraries are screened using the DNA as a probe to obtain a DNA encoding the protein.

A biosensor using the Surface Plasmon Resonance phenomenon may be used as a means for detecting or quantifying the bound compound in the present invention. When such a biosensor is used, the interaction between a protein of the invention and a test compound can be observed in real-time as a surface plasmon resonance signal, using only a minute amount of proteins without labeling (for example, BIAcore, Pharmacia). Therefore, it is possible to evaluate the binding between a protein of the invention and a test compound using a biosensor such as BIAcore.

Methods of screening molecules that bind when an immobilized protein of the present invention is exposed to synthetic chemical compounds, natural substance banks, or a random phage peptide display library, and methods of screening using high-throughput based on combinatorial chemistry techniques (Wrighton N C., Farrel F X., Chang R., Kashyap A K., Barbone F P., Mulcahy L S., Johnson D L., Barret R W., Jolliffe L K., and Dower W J. (Jul. 26, 1996) "Small peptides as potent mimetics of the protein hormone erythropoietin" Science (UNITED STATES) 273, 458-64; Verdine G L. (Nov. 7, 1996) "The combinatorial chemistry of nature." Nature (ENGLAND) 384, 11-13; Hogan J C Jr. (Nov. 7, 1996) "Directed combinatorial chemistry." Nature (ENGLAND) 384, 17-9) are well known to those skilled in the art as methods for isolating not only proteins but also chemical compounds that bind to a protein of the present invention (including agonist and antagonist).

A protein of the present invention is also useful for the screening for compounds that control the transcriptional regulation activity of the protein. More specifically, the protein of the present invention is used in the method of screening for compounds that control the transcriptional regulation activity of the protein of the present invention comprising the steps of: (a) contacting the protein of the present invention or partial peptides thereof with a test sample expected to contain a compound that controls the transcriptional regulation activity of the protein; (b) detecting the transcriptional regulation activity of the protein or partial peptides thereof; and (c) selecting the compound that decreases or increases the activity as compared with that observed in the absence of the test sample (control).

The screening can be conducted as follows, for example, using the mammalian One-Hybrid System (see Example 8).

First, a vector which expresses a protein of the present invention as a fusion protein with a known peptide having DNA binding activity, such as the DNA binding domain of GAL4 (designated as "primary vector"), and a vector wherein a reporter gene is linked in an expressible manner downstream of the sequence to which the peptide with the DNA binding activity binds (designated as "secondary vector") are constructed. The primary and secondary vectors are introduced into the cells and the reporter activities are detected. Examples of cells to be used in the method include MG63, HeLa, and 293. In the secondary vector, an appropriate promoter (e.g., CMV promoter), whose transcriptional activity regulated by the protein of the present invention is to be detected, can be used. The reporter activity detected by the introduction of the primary and secondary vectors is compared with that obtained without the primary vector. When the reporter activity changes upon the introduction of the vector as compared with that observed in the absence of the primary vector, the change is evaluated as the "transcriptional regulation activity" of the protein of the present invention.

Next, the reporter activity is detected, in a similar manner, except contacting the cells retaining the primary and secondary vectors with a test sample. The samples to be tested are not limited, but may be cell extracts, culture supernatants, fermented products of microorganisms, extracts of marine organisms, plant extracts, purified or partially purified proteins, peptides, non-peptide compounds, synthetic low molecular compounds, or natural compounds. Further, the test samples can be compounds isolated by the screening for a compound that binds to a protein of the present invention described above. Because of the detection, a test sample can be determined as a compound that controls the transcriptional regulation activity of a protein of the present invention, when the "transcriptional regulation activity" of the protein of the present invention increases or decreases in accordance with the contact of the test sample.

Compounds that can be isolated by the screening method of this invention may be applied to treatment of diseases caused by expressional or functional abnormalities of a protein of this invention, or diseases that may be treated by regulating the activity of a protein of this invention. Compounds isolated by the screening method of this invention, wherein the structure of compounds is partially altered via addition, deletion, and/or replacement, are also included as compounds that bind to a protein of this invention.

When a protein or peptide of the present invention, or a compound that can be isolated by the screening method of the present invention is used as a pharmaceutical for humans and other animals, such as, mice, rats, guinea pigs, rabbits, chicken, cats, dogs, sheep, pigs, bovines, monkeys, baboons, chimpanzees, the isolated compound can be administered not only directly, but also as dosage forms using known pharmaceutical preparation methods. For example, according to the need, the drugs can be taken orally as sugarcoated tablets, capsules, elixirs and microcapsules; or non-orally in the form of injections of sterile solutions or suspensions with water or any other pharmaceutically acceptable liquid. For example, the compounds can be mixed with pharmacologically acceptable carriers or medium, specifically, sterilized water, physiological saline, plant-oil, emulsifiers, suspending agent, surface-active agent, stabilizers, flavoring agents, excipients, vehicles, preservatives and binders, into a unit dose form required for generally accepted drug implementation. The amount of active ingredient in these preparations makes a suitable dosage within the indicated range acquirable.

Examples of additives which can be incorporated into tablets and capsules are: binders such as gelatin, corn starch, tragacanth gum and gum acacia; excipients such as crystalline cellulose; swelling agents such as corn starch, gelatin and alginic acid; lubricants such as magnesium stearate; sweeteners such as sucrose, lactose or saccharin; flavoring agents such as peppermint, *Gaultheria adenothrix* oil and cherry. When the unit dosage form is a capsule, a liquid carrier such as oil can also be included in the above ingredients. Sterile composites for injection can be formulated following normal drug implementations using vehicles such as distilled water used for injections.

Physiological saline, glucose, and other isotonic liquids including adjuvants, such as D-sorbitol, D-mannose, D-mannitol, and sodium chloride, can be used as aqueous solutions for injections. These can be used in conjunction with suitable solubilizers, such as alcohol, specifically ethanol; polyalcohols such as propylene glycol and polyethylene glycol; and non-ionic surfactants such as Polysorbate 80 (TM) and HCO-50.

Sesame oil or Soy-bean oil can be used as a oleaginous liquid and may be used in conjunction with benzyl benzoate or benzyl alcohol as solubilizers. They further may be formulated with a buffer such as phosphate buffer and sodium acetate buffer, a pain-killer such as procaine hydrochloride, a stabilizer such as benzyl alcohol and phenol, and an anti-oxidant. The prepared injection may be filled into a suitable ampule.

Methods well known to one skilled in the art may be used to administer the pharmaceutical compounds of the present invention to patients, for example as intra-arterial, intravenous, or percutaneous injections and as intranasal, transbronchial, intramuscular percutaneous, or oral administrations. The dosage varies according to the body-weight and age of a patient and the administration method, but one skilled in the art can suitably select them. If the compound can be encoded by a DNA, the DNA can be inserted into a vector for gene therapy to perform the therapy. The dosage and method of administration vary according to the body-weight, age, and symptoms of a patient, but one skilled in the art can select them suitably.

Although there are some differences according to the subject, subject organ, symptoms, and administration method, the dose of a protein of the present invention to be injected to a normal adult (weight 60 kg) is, for example, about 100 µg to about 20 mg per day.

Although there are some differences according to the symptoms, the dose of a compound that binds with a protein of the present invention and regulates the activity of the protein is considered to be about 0.1 mg to about 100 mg per day, preferably about 1.0 mg to about 50 mg per day, and more preferably about 1.0 mg to about 20 mg per day, when administered orally to a normal adult (weight 60 kg).

When administering parenterally in the form of an injection to a normal adult (weight 60 kg), although there are some differences according to the patient, target organ, symptoms and method of administration, it may be convenient to intravenously inject usually a dose of about 0.01 mg to about 30 mg per day, preferably about 0.1 to about 20 mg per day, and more preferably about 0.1 to about 10 mg per day. In addition, in the case of other animals too, it is possible to administer an amount converted to 60 kgs of body-weight or an amount converted to body surface.

BRIEF DESCRIPTION OF THE DRAWINGS

FIG. 1 depicts the cDNA sequence and amino acid sequence of murine 285 (m285), SEQ ID NO: 1 and SEQ ID NO:2, respectively. Three zinc fingers are indicated in italic, and proline-rich region and alanine-rich region are underlined with solid and dotted lines, respectively.

FIG. 2 depicts the comparison of the amino acid sequences of murine 285 (SEQ ID NOS:27-44) and the three zinc finger domains of the Sp family transcription factors and Sp family-like transcription factors. In the figure, amino acid residues identical to those of Sp1 are indicated as "-". The zinc finger domains are underlined and conserved cysteine and histidine residues are shaded in gray.

FIG. 3 depicts the comparison of the N-terminal amino acid sequences of murine 285 (SEQ ID NO: 48), murine Sp1 (SEQ ID NO:45), human Sp2 (SEQ ID NO:46), and human Sp4 (SEQ ID NO:47). Amino acid residues conserved in three of the four molecules are shown in gray, and those conserved in all molecules are indicated by reversed characters.

FIG. 4 depicts photographs demonstrating the expression of m285 in CL6 by RT-PCR upon the induction of myocardial differentiation. DMSO-unstimulated cells are designated as 0 day.

FIG. 6 depicts the cDNA sequence and amino acid sequence of human 285 (h285), SEQ ID NO: 3 and SEQ ID NO: 4, respectively. The three zinc fingers are indicated in italic, and the proline-rich region and alanine-rich region are underlined with solid and dotted lines, respectively.

FIG. 7 depicts the comparison of amino acid sequences of murine and human 285, SEQ ID NO: 2 and SEQ ID NO: 4, respectively. The three zinc fingers and proline-rich regions are underlined with waved and solid lines, and the alanine-rich regions are boxed. They share a homology of 97.5% at the amino acid sequence level.

BEST MODE FOR CARRYING OUT THE INVENTION

Figure 5:
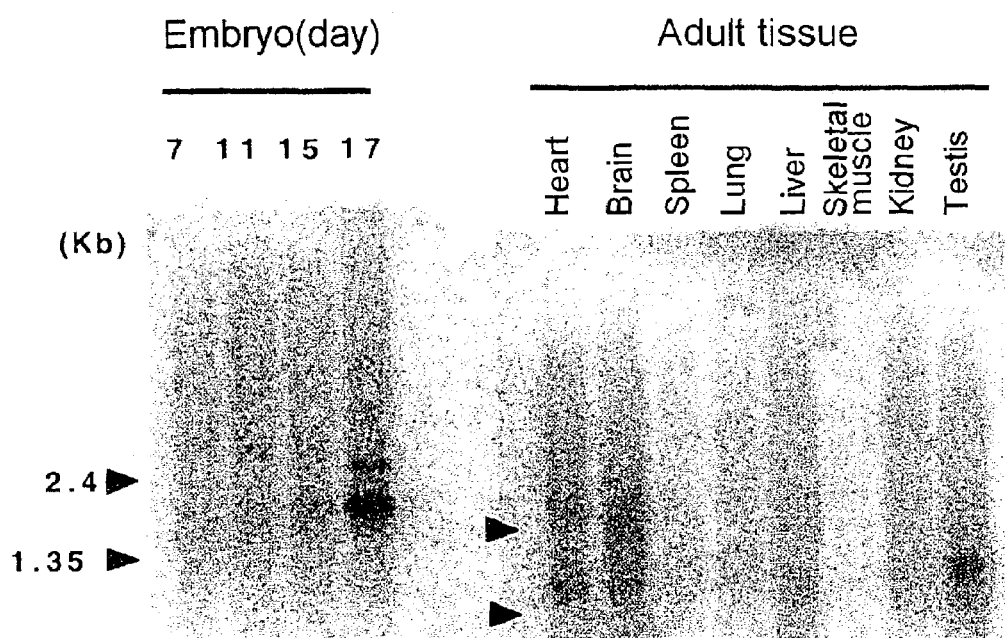
FIG. 5 depicts photographs demonstrating the tissue distribution of m285 expression by murine Northern blot analysis.

The present invention will be explained in detail below with reference to the following Examples, however, it is not construed as being limited thereto.

EXAMPLE 1

Isolation of m285 Gene Fragment

Differentiation of undifferentiated murine embryonal carcinoma cell line, P19, to various neuronal cells, smooth muscle cells, cardiomyocytes, and such can be induced by stimulation with various stimuli (DMSO, retinoic acid, etc.) (Bain G. et al. (1994) Bioessays 16, 343-348; McBurney M W. (1993) Int. J. Dev. Biol. 37, 135-140). CL6 cell is an undifferentiated cell line established from P19 (Habara-Ohkubo A. (1996) Cell Struct. Funct. 21, 101-110). The CL6 cells can be efficiently differentiated to cardiomyocyte-like cells by adding 1% DMSO to the cell culture media under an adherent condition, while P19 must be maintained in a floating condition to form an emryoid body for the induction of differentiatiation. The CL6 cells express cardiac muscle gene, such as cardiac α and β-HMC, approximately 8 days after the stimulation by 1% DMSO, and start a synchronized pulsation approximately 10 days after the stimulation. The present inventors searched for genes involved in cardiac muscle differentiation as described below using the differentiation induction system of CL6 cells.

The culture of CL6 cells was carried out according to the method of Habara-Ohkubo. Cells before and 4 days after adding 1% DMSO were treated with trypsin, were collected, and total RNA was obtained using RNeasy total RNA isolation kit (QIAGEN). PolyA+ RNA was obtained from total RNA using Mini-Oligo (dT) Spin Column Kit (5prime-3prime, Inc.) The obtained polyA+ RNA samples from CL6 cells before (A) and 4 days after (B) adding with 1% DMSO were used as templates of the subtraction PCR method. It was conducted by subtracting (A) from (B), using CLONTECH PCR select cDNA Subtraction Kit (CLONTECH) according to the manufacturer's instruction. The obtained subtracted PCR products were subcloned into pCR Blunt II vector using Zero blunt TOPO PCR Cloning Kit (invitrogen). Colonies retaining recombinants were amplified by colony-PCR described below, and the nucleotide sequences were confirmed using nested primer 1 (nP1) and nested primer 2R (nP2R) (CLONTECH). As a result, many gene fragments whose expression increases in accordance with the induction of differentiation to cardiomyocyte were obtained. Among these obtained gene fragments, fragment PS40-285 was further analyzed (see, Example 2-).

Colony PCR of the present Examples was carried out as follows. Colonies retaining the recombinants were directly suspended in 20 μl PCR reaction mixture comprising SPORT FW (5'-TGT AAA ACG ACG GCC AGT-3'/SEQ ID NO: 5), SPORT RV (5'-CAG GAA ACA GCT ATG ACC-3'/SEQ ID NO: 6), and KOD dash polymerase; and PCR was carried out at a condition of 94° C. for 1 minute, and 32 cycles of 96° C. for 15 seconds, 55° C. for 5 seconds, and 72° C. for 25.seconds. The amplified PCR products were confirmed by agarose gel electrophoreses and purified as needed using Microspin S-300, S-400 gel filtration (Pharmacia) or using Multiscreen HV plate (Millipore)+BioGel-P60 (BioRad) to prepare templates for the sequencing reaction.

Determination of nucleotide sequences of the present Examples was carried out as follows. PCR products of colony PCR, RT-PCR, and such were used as the templates of a sequencing reaction. After the PCR, products were confirmed by agarose gel electrophoreses, and the objective PCR products were either cut out from the gel when impurities were present, or those without contaminants were purified by gel filtration. Cycle sequencing using BigDye Terminator Cycle Sequencing FS ready Reaction Kit (Perkin-Elmer) was carried out as the sequencing reaction. Unreacted primers, nucleotides, and such were removed by 96 well precipitation HL kit (AGTC), and the nucleotide sequences were determined using ABT 377 or ABI 377XL DNA Sequencer (Perkin-Elmer).

EXAMPLE 2 cDNA Cloning of m285 Gene

Using mouse 10.5 dpc embryo cDNA plasmid library as a template, cDNA containing total ORF of m285 was cloned based on the nucleotide sequence of a gene fragment PS40-285 (FIG. 1). The nucleotide sequence of the cloned m285 cDNA containing total ORF was determined. Determination of the nucleotide sequence was carried out as follows.

According to the nucleotide sequence of the subtraction clone PS40-285, primers, 285-A (5'-CAG CCC TGG GTA AAA TGT AAG TC-3'/SEQ ID NO: 7), 285-B (5'-TCG AGG TAG CTG ACA AAG AGT AAC-3'/SEQ ID NO: 8), 285-C (5'-TCA CCA GTG CAG GGA TCT ACA AA-3'/SEQ ID NO: 9), and 285-D (5'-GCA GTC AGG TGT CTT GGT CTG ATT-3'/SEQ ID NO: 10), were synthesized on Beckman automatic DNA synthesizer. SuperScript Mouse 10.5 day embryo cDNA library (GIBCO) was added to 5 ml LB-Amp medium at a concentration of $2.1 \times 10^3$ clones, cultured at 30° C., and then plasmids were obtained using QIAspin mini prep kit (QIAGEN). Using the plasmids as a template, reaction by Advantage cDNA polymerase (CLONTECH) was carried out with following primers and cycles.

Specifically, following primers were used for the reaction: 285-A+SPORT FW (1st. 3' RACE) and 285-C+SPORT T7 (5'-TAA TAC GAC TCA CTA TAG GG-3'/SEQ ID NO: 11) (nested 3' RACE) as 3' RACE primers, and 285-B+SPORT RV (1st. 5' RACE) and 285-D+SP6 (5'-ATT TAG GTG ACA CTA TAG A-3'/SEQ ID NO: 12) (nested 5' RACE) as 5' RACE primers. The first RACE was carried out at a condition of 95° C. for 1 minute, and 30 cycles of 96° C. for 15 seconds, 63° C. for 15 seconds, and 68° C. for 3 minutes; and the nested RACE was carried out under the same conditions except that the cycle number was 15. The nucleotide sequences of nested RACE products were determined using primers that were used for the RACE. As for the 5' RACE products, the nucleotide sequences were determined using 285-E (5'-TTC TCG CCC GTG TGA GTC CGC A-3'/SEQ ID NO: 13), and 285-F (5'-TCC AGA CTT TTC CAC CCT TGG ACT-3'/SEQ ID NO: 14).

As a result, m285 was revealed to comprise 1830 bases that encode 398 amino acids. The amino acid sequence contained three zinc finger domains in its C-terminus, and a proline-rich rich and an alanine-rich region in the middle of the sequence. (FIG. 1).

Next, BLAST database search of the m285 cDNA was conducted, which revealed that it has a high homology with a human UniGene clone (NCBI human UniGene clone No.: Hs.145921) and a human HTG clone (GenBank accession No.: AC007405), and thus it was discovered that m285 is the mouse counterpart of these clones. However, no known gene with high homology covering the whole gene could be found in the database; and thus, it was determined to be a novel gene. Because of database search with the amino acid sequence of m285, three zinc finger domains that were located in the C-terminus showed very high homology with the Sp family transcription factors (FIG. 2). Among these factors, Sp4 showed an especially high homology, which reached 88.6% identity in the three zinc finger domains. In addition, in the N-terminus, it had a completely identical region (though only 11 amino acid residues) to Sp1, Sp2, and Sp4 (FIG. 3). However, other regions besides those described above did not show homology to the Sp family genes. Further, no known gene with high homology covering the whole m285 sequence could be found; thus m285 was revealed to be a novel gene with three zinc finger domains.

EXAMPLE 3 m285 Gene Expression in CL6 Differentiation Induction System

CL6 is a cell line isolated from undifferentiated embryonal carcinoma cell line, P19, and upon differentiation induction by DMSO, it differentiates from the undifferentiated character to a cardiomyocyte-like cell in approximately 10 days. m285 was obtained as a gene whose expression increases in accordance with the induction of cardiomyocyte differentiation of CL6 (4 days after DMSO stimulation) Therefore, to analyze the m285 gene expression in the CL6 differentiation induction system by RT-PCR, RNAs were isolated from undifferentiated CL6 (without the differentiation induction with DMSO), and CL6 cells 4 days, 8 days, and 12 days after the differentiation induction with DMSO. At the same time, RNA isolated from adult mouse heart was also analyzed. The RT-PCR was carried out as follows.

Using the total RNA prepared from CL6 cells before addition of DMSO, and cells 4 days, 8 days, and 12 days after the addition of 1% DMSO, and mouse heart total RNA of C3H/He (Nippon Gene); SuperScript II (GIBCO) as RTase; and $(dT)_{30}VN$ primers, cDNAs, which are used as templates of RT-PCR, were synthesized. The RT-PCR with Advantage cDNA polymerase using 285-A and 285-B primer sets and, as a control, G3PDH 5' (5'-GAG ATT GTT GCC ATC AAC GAC C-3'/SEQ ID NO: 15) and G3PDH 3' (5'-GTT GAA GTC GCA GGA GAC AAC C-3'/SEQ ID NO: 16) primer set was carried out at a condition of 95° C. for 1 minute, and 28 cycles (20 cycles for G3PDH) of 96° C. for 15 seconds, 60° C. for 15 seconds, and 68° C. for 30 seconds.

Because of the RT-PCR, m285 was revealed to be transiently expressed in only CL6 cells 4 days after the differentiation induction with DMSO (FIG. 4). No expression was observed in CL6 cells before differentiation induction, those eight or more days after the differentiation induction, and in adult mouse heart.

EXAMPLE 4

Tissue Distribution of m285 Gene Expression

Next, m285-expressing tissues were searched by Northern blot analyses. PCR with 285-Eand285-Fusing the 5' RACE products of Example 3 as a template was carried out to obtain a product of approximately 0.9 kb. The PCR product was labeled with [$\alpha$-$^{32}$P]dcTp using Megaprime DNA labelling system (Amersherm), and then unreacted [$\alpha$-$^{32}$p]dCTP was removed to prepare m285 probe. Using Mouse Multiple Tissue Northern (MTN) blot and Mouse Embryo MTN blot (CLONTECH), hybridization was carried out at 68° C. in ExpressHyb Hybridization Solution (CLONTECH) according to the manufacturer's instruction. After exposing to imaging plates, analyses were accomplished using BAS2000 imaging analyzer.

As a result, in the prenatal period, a very high expression of m285 was observed in 17 dpc murine embryo; and little expression is observed in 7 dpc, 11 dpc, and 15 dpc embryos. In the adult mice, expression in testis, and weak expression in brain, heart, liver, and kidney tissues were detected (FIG. 5). Considering the result with the above-described expression patterns in CL6 differentiation induction system, m285 is expected to be somehow involved in the late stage of development, because of its very high expression in 17 dpc embryo.

EXAMPLE 5 cDNA Cloning of h285 Gene

Based on the nucleotide sequence of m285, and the above-mentioned human UniGene clone (Hs.145921; NCBI human UniGene clone number) and human HTG clone (AC007405; GenBank accession number), cloning of h285 gene was carried out as follows.

Using human fetal brain Marathon ready cDNA (CLONTECH) as a template, RACE was carried with either 285-J (5'-CTT GC (A/G)CA GTA CCA GAG CCA GAT-3'/SEQ ID NO: 17) and AP1 (1st. 3' RACE), or 285-hC (5'-AAG AAG AAG CAG CAC GTG TGC CAC-3'/SEQ ID NO: 18) and AP2 (nested 3' RACE) using Advantage cDNA polymerase following procedures described below. Specifically, the first RACE was carried out under a condition of 95° C. for 1 minute, and 35 cycles of 96° C. for 15 seconds, 63° C. for 15 seconds, and 68° C. for 2 minutes; and nested RACE was carried out under the same condition except for the cycle number being 20.

Using rTaq (TaKaRa), dA was added to the nested RACE products to subclone the products into pCR 2.1 TOPO (invitrogen), and determine their nucleotide sequences.

RT-PCR with PCRx system-Platinum Taq (GIBCO) using human fetal brain cDNA (CLONTECH) as a template, and 28.5-hG (5'-GGC GTC CCG CTC CGC AGC CA-3'/SEQ ID NO: 19) and 285-hB (5'-CCG GCC TCA GCG ACT TTG AGC TT-3'/SEQ ID NO: 20) as primers was carried out under a condition of 95° C. for 1 minute, and 40 cycles of 96° C. for 15 seconds, 58° C. for 15 seconds, and 72° C. for 1.5 minutes.

Following the addition of dA to the RT-PCR products using rTaq (TaKaRa), the products were subcloned into pCR 2.1 TOPO (invitrogen) to determine their nucleotide sequences (FIG. 6).

As a result, the obtained h285cDNA, as same as m285, was considered to encode 398 amino acids. According to a comparison with m285, h285 showed 91.1% and 97.5% homology at the nucleotide sequence level within the coding region and the amino acid sequence level, respectively (FIG. 7). The cDNA sequence was almost identical to human UniGene clone (Hs.145921) and human HTG clone (AC007405) (these sequences contain several bases of addition/deletion, which seem to be the result of sequencing errors). The amino acid sequence of h285 comprised, similarly to m285, three zinc finger domains in its C-terminus that share a very high homology to those of the Sp family, N-terminal 11 amino acid residues completely identical to those in Sp1, Sp2, and Sp4, and proline-rich and alanine-rich regions in the middle (FIG. 7).

No known gene with high homology to h285 covering the whole region could be found as in the case of m285, and h285 was revealed to be a novel gene.

EXAMPLE 6

Intracellular Localization of m285

Generally, transcription factors diversely regulate gene expressions by binding to DNA. Although some transcription factors exist that usually exist in the cytosol, translocate to the nucleus by certain signal/stimuli, and regulate transcription, many of the transcription factors including the Sp family transcription factors localize in the nucleus of the cell. Therefore, intracellular localization of the cloned m285 was examined.

Plasmids that express full-length m285 (285F; amino acid residues 1 to 398), N-terminal region of m285 (285N; amino acid residues 1 to 278), and C-terminal region of m285 (285C; amino acid residues 271 to 398) as EGFP fusion proteins were constructed. 285N comprises the N-terminal 11 amino acid residues that are identical to those of Sp1, Sp2, and Sp4, a proline-rich region and an alanine-rich region; whereas 285C comprises the C-terminal three zinc finger domains that share a very high homology to those of the Sp family. Plasmid constructions were carried out as follows. First, 285EcoRI-N (5'-GAA TTC CCT TCA AGC AGT AGC CAT GGC CG-3'/SEQ ID NO: 21), 285EcoRI-P (5'-GAA TTC CTT TGC ATA CCA GAG CGA GAT-3'/SEQ ID NO: 22), 285SalI-K (5'-GTC GAC ATC TGG CTC TGG TAC TGT GCA AAG-3'/SEQ ID NO: 23), and 285SalI-M (5'-GTC GAC AGT GTC CCG GTG CGC TCA TAG GTC-3'/SEQ ID NO: 24), derived from m285 were synthesized. Then, cDNA was synthesized from total RNA that was isolated from CL6 cells 4 days after DMSO stimulation, and RT-PCR was carried out using 285EcoRI-N+285SalI-M (285F), 285EcoRI-N+285SalI-K (285N), and 285EcoRI-P+285SalI-K (285C). Following the addition of dA-to the RT-PCR products with rTaq (TaKaRa), the products were subcloned into pCR 2.1 TOPO, respectively.

pCR2.1-285F, 285N, and 285C were digested with EcoRI and SalI, and obtained fragments were subcloned into pGEX 4T-3 (Pharmacia) in frame. JM-109was transformed with the plasmids and GST fusion proteins (GST-285F, GST-285N, and GST-285C) were obtained following the manufacturer's protocol. The fusion proteins were subjected to DNA binding assay described below.

Similarly, EcoRI-SalI fragments of pCR2.1-285F, 285N, and 285C were subcloned into pEGFP-C1 (CLONTECH) in frame (pEGFP-285F, pEGFP-285N, and pEGFP-285C).

Next, thus constructed EGFP fusion protein expression plasmids were transfected into CL6 cells using FuGENE6 (Roche Diagnostics) according to the manufacturer's protocol for transient expression of the fusion proteins; and after 48 hours, cells were observed under fluorescence microscopy. At the same time, a plasmid that expresses EGFP alone was also transfected in the same way.

Figure 8:
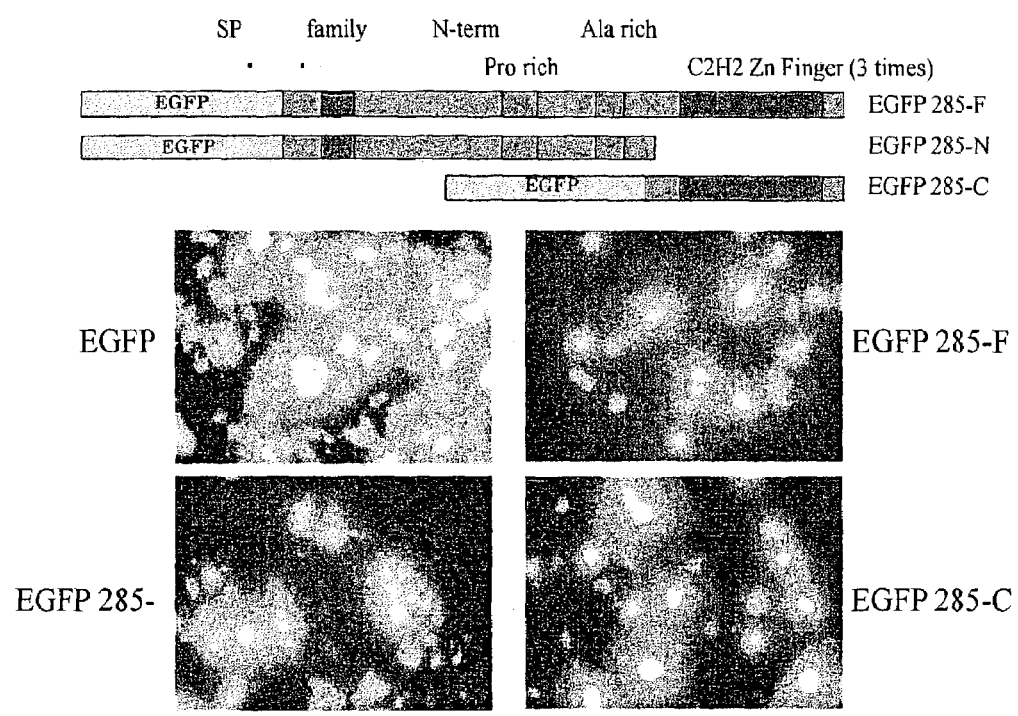
FIG. 8 depicts photographs demonstrating intracellular localization of m285 in CL6 cells.

As a result of the observation using fluorescence microscopy, fluorescence was observed from the whole cells that were transfected with EGFP alone or EGFP-285N, while the fluorescence could be only detected in the nucleus for those transfected with EGFP-285F and EGFP-285C (FIG. 8). Thus, m285 was revealed to be a protein localized in the nucleus, which nuclear translocation of the protein requires its C-terminal region including three zinc finger domains.

EXAMPLE 7

DNA Binding Activity

Sp1 is known to bind to a GC-box through its three zinc finger domains. The m285 cloned in the present invention has three zinc finger domains that share a very high homology with the Sp family, and therefore the protein was expected to bind to a GC-box. Thus, 285F, 285N, and 285C were expressed as GST fusion proteins in $E.\ coli$ to examine their binding to a GC-box. GST fusion proteins purified with glutathione Sepharose, and as the GC box a DNA probe having the nucleotide sequence in the Waf-1 promoter region which sequence binds to Sp1 were used. DNA probe was prepared by labeling ds-(5'-TCG AAA GGA GGC GGG ACC CGA GCT-3'/SEQ ID NO: 25) containing a GC-box sequence with 33-P. The DNA probe was reacted with GST-285F, GST-285N, and GST-285C described above in EMSA buffer (20 mM HEPES, 40 mM KCl, 6 MM $MgCl_2$, 1 mM EGTA, 1 mM DTT, 0.1% NP-40, 10% Glycerol, 0.15% BSA, 25 ng/μl sonicated salmon sperm DNA) for 20 minutes. To examine the presence of competitive inhibition, either an unlabeled GC-box DNA probe or unlabeled mutant GC-box DNA probe (ds-(5'-TCG AAA GGA GTT TTG ACC CGG AGC T-3'/ SEQ ID NO: 26)) was further added to a similar reaction system. Recombinant Sp1 was used as a positive control. The reactants were electrophoresed on 5% acrylamide gel and were exposed to imaging plates. Analyses were performed using BAS2000 imaging analyzer.

Figure 9:
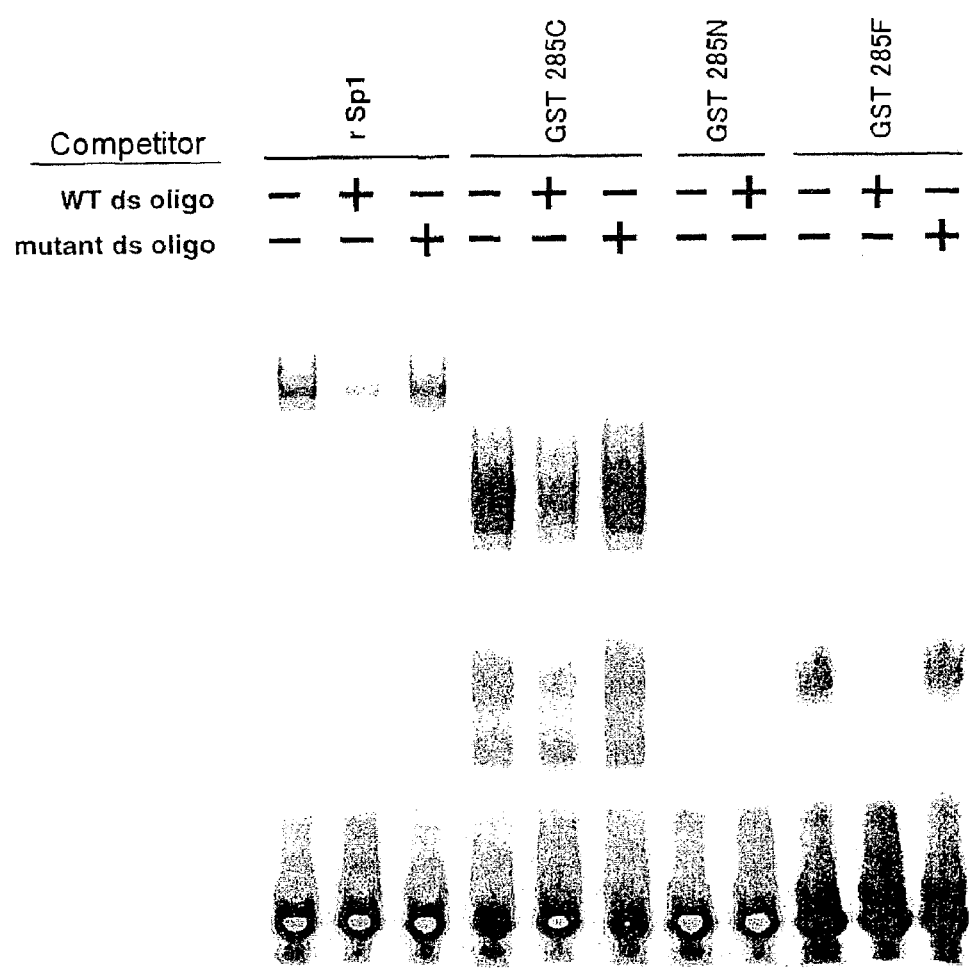
FIG. 9 depicts an electrophoretogram of the binding assay between-GST fusion 285F, 285N, and 285C to the 33-P labeled GC-box DNA probes. Unlabeled ds oligo was used as the competitor.

As a result of gel shift assay, bands that were considered to correspond to DNA-protein complex were observed when GST-285F, GST-285C, or recombinant Sp1 were reacted with the 33-P labeled GC-box DNA probe (FIG. 9; lanes 1, 4, and 9). No complex b and could be observed for GST-285N reacted with the GC-box DNA probe (FIG. 9; lane 7). The addition of unlabeled GC-box DNA probe vanished or decreased the complex bands of GST-285F, GST-285C, or recombinant Sp1, and the GC-box DNA probe (FIG. 9; lanes 2, 5, and 10). Further, the addition of unlabeled mutant GC-box DNA probe to a similar reaction system had no effect on the complex bands of GST-285F, GST-285C, or recombinant Sp1, and the GC-box DNA probe (FIG. 9; lanes 3, 6, and 11). These results indicate that m285binds specifically to a GC-box sequence through its C-terminal region comprising three zinc finger domains.

EXAMPLE 8

Transcriptional Regulation by Mammalian One-Hybrid System

Figure 10:
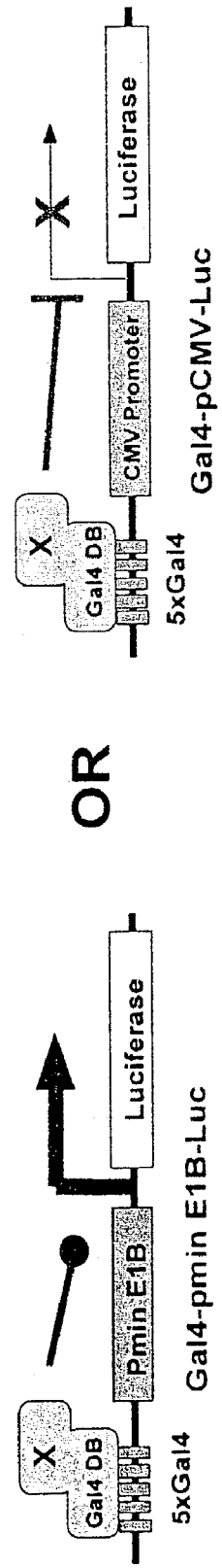
FIG. 10 depicts schematic illustrations of the activation assay and repression assay.

The Sp family transcription factors are known to enhance transcription through their glutamine-rich regions; however, transcriptional repression through regions other than glutamine-rich region has also been reported for Sp1 and Sp3. Thus, the mechanism of the transcriptional regulation (activation/repression) by the newly cloned 285 was examined by the mammalian One-Hybrid System (FIG. 10).

Vectors expressing the Gal4 DNA binding domain and 285F, 285N, or 285C as fusion proteins were constructed by subcloning EcoRI-SalI fragments of pCR2.1-285F, 285N, and 285C into pM (CLONTECH) in frame (pM-285F, pM-285N, and pM-285C). They were used as assay plasmids.

Activation assay was performed using pG5-Luc (5× Gal4 binding site—E1B minimal promoter—Luciferase; Sowa Y. et al. (1999) Cancer Res. 59: 4266-4270) and pM-Sp1 (Gal4 DNA binding domain —Sp1; Sowa Y. et al. (1999) Cancer Res. 59: 4266-4270) as a reporter plasmid and positive control plasmid, respectively. Repression assay was performed using pKO-114 (5×Gal4 binding site—CMV promoter—Luciferase) as a reporter plasmid. pKO-114 was constructed by digesting pGL3-basic vector (Promega) with SmaI and HindIII, and then inserting into the site 5×Gal4 binding site (SmaI-XbaI fragment) derived from pG5-Luc and CMV promoter derived from pcDNA3.1-HisA (Invitrogen) (SpeI-HindIII fragment). pRL/SV40 (Promega) was used as an internal control plasmid in both assays.

Figure 11:
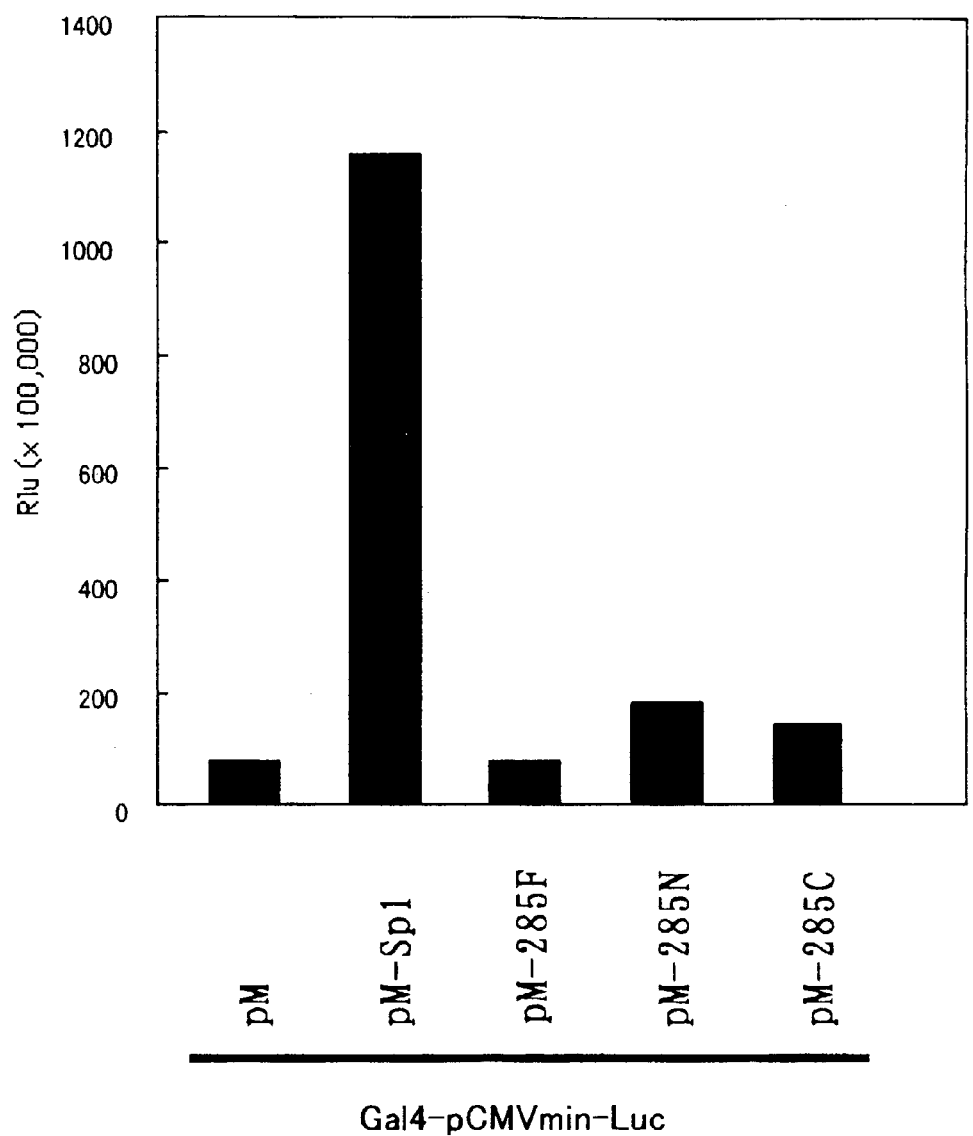
FIG. 11 depicts a graph demonstrating the result of the activation assay. None of the tested plasmids activated the E1B minimal promoter.
Figure 12:
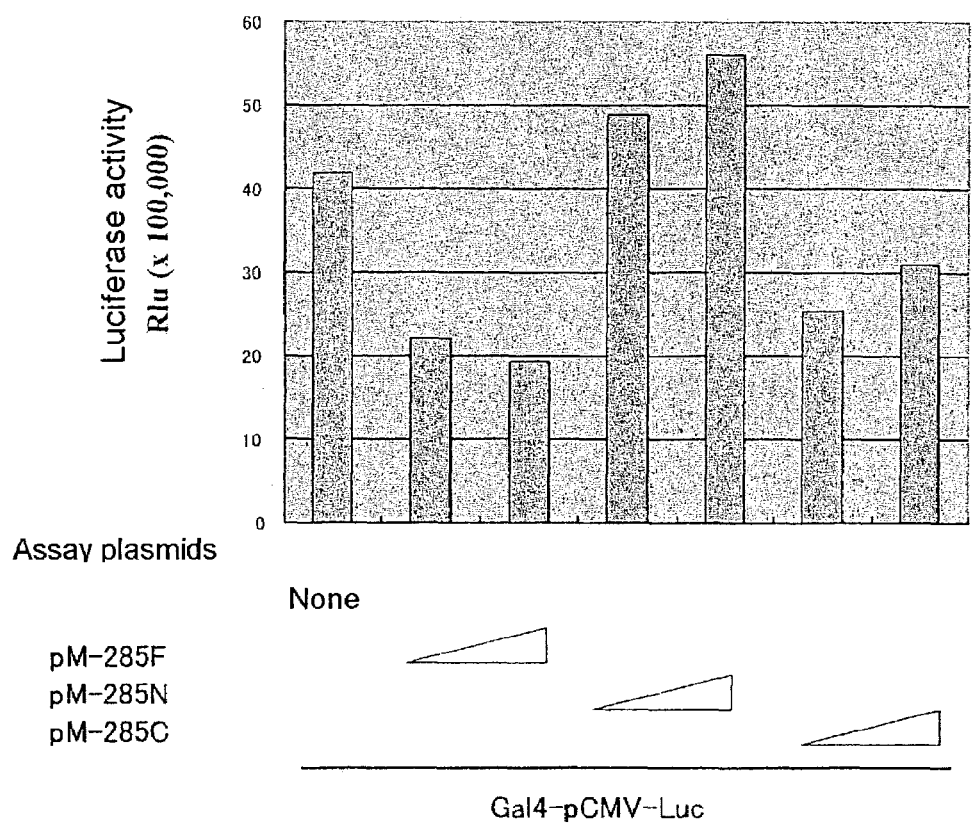
FIG. 12 depicts a graph demonstrating the result of the repression assay. 285F repressed CMV promoter activity in a dose dependent manner.

MG63 cells (obtained from Kyoto Prefectural University) were seeded onto 12 well plates at 8×10^4 cells/well and cultured. On the next day, MG63 cells were transfected with the assay plasmid (or positive control plasmid), reporter plasmid, and internal control plasmid, using Superfect (QIAGEN). After 2 days, the luciferase activities were measured using Dual-Luciferase Reporter Assay System (Promega) According to the result of the activation assay (FIG. 10), it was revealed that 285does not activate the transcription of CMV minimum promoter in MG63 cells (FIG. 11). To the contrary, the repression assay (FIG. 10) revealed that 285 represses the transcriptional activity of CMV promoter in MG63 cells (FIG. 12). The level of the repression was almost equal to that of KRAB (derived from KOX) used as a control.

Thus, it was revealed that 285 functions as a transcription factor.

INDUSTRIAL APPLICABILITY

The present invention provides genes encoding a novel transcription factor that is considered to belong to the Sp1 transcription factor family. Proteins encoded by such genes are expected to regulate the transcription of genes by binding to a GC-box through their zinc finger domains. The genes and proteins of the present invention are useful as targets for developing therapeutic agents.

The invention claimed is:

1. An isolated mammalian DNA selected from the group consisting of:
   (a) a DNA encoding a protein comprising the amino acid sequence of SEQ ID NO: 2or 4;
   (b) a DNA containing the full length coding region of the nucleotide sequence of SEQ ID NO: 1 or 3;
   (c) a DNA encoding a protein comprising the amino acid sequence that has a sequence homology of 95% or more to the entirety of the amino acid sequence of SEQ ID NO: 2 or 4; and wherein the protein represses the transcriptional activity of a CMV promoter and has binding activity to a GC-box of the Waf-1 promoter;
   (d) a DNA encoding a protein fragment comprising the amino acid sequence of residues 271 to 398 of SEQ ID NO: 2; and
   (e) a DNA consisting of nucleotides 811-1194 of SEQ ID NO: 3.

2. A recombinant vector into which the DNA of claim 1 is inserted.

3. An isolated transformed cell modified to contain the DNA of claim 1.

4. A method for producing a protein or protein fragment thereof which is a transcription factor that represses a CMV promoter wherein the method comprises the steps of culturing a transformed cell modified to contain an isolated mammalian DNA selected from the group consisting of:
   (a) a DNA encoding a protein comprising the amino acid sequence of SEQ ID NO: 2 or 4;
   (b) a DNA containing the full length coding region of the nucleotide sequence of SEQ ID NO: 1 or 3;
   (c) a DNA encoding a protein comprising the amino acid sequence that has a sequence homology of 95% or more to the entirety of the amino acid sequence of SEQ ID NO: 2 or 4; and wherein the protein represses the transcriptional activity of a CMV promoter and has binding activity to a GC-box of the Waf-1 promoter;
   (d) a DNA encoding a protein fragment comprising the amino acid sequence of residues 271 to 398 of SEQ ID NO: 2; and
   (e) a DNA consisting of nucleotides 811-1194 of SEQ ID NO: 3, expressing a protein or protein fragment encoded by the DNA of any of (a)-(e) contained within said transformed cell, and recovering the expressed protein or protein fragment from said transformed cell or a culture supernatant thereof.

5. An isolated DNA encoding a protein comprising the amino acid sequence of SEQ ID NO: 2 or 4.

6. An isolated DNA containing the full length coding region of the nucleotide sequence of SEQ ID NO: 1 or 3.

* * * * *

SEQUENCE LISTING

```
<160> NUMBER OF SEQ ID NOS: 26

<210> SEQ ID NO 1
<211> LENGTH: 1830
<212> TYPE: DNA
<213> ORGANISM: Mus musculus
<220> FEATURE:
<221> NAME/KEY: CDS
<222> LOCATION: (75)..(1268)

<400> SEQUENCE: 1
agcttgggcc cctcgaggga tcctctagag cggccgccyy ctgctccaca gcgagcggcc        60
ttcaagcagt agcc atg gcc gct gtg gcc gtc ctc cgg aac gac tca ctg       110
              Met Ala Ala Val Ala Val Leu Arg Asn Asp Ser Leu
                1               5                  10 cag gcc ttc ctc cag gac cgc acc ccc agc gcc tcc ccg gac ctg ggc       158
Gln Ala Phe Leu Gln Asp Arg Thr Pro Ser Ala Ser Pro Asp Leu Gly
         15                  20                  25 aag cac tcg ccc ctg gcg ctg ctg gcc gcc acc tgt agc cgg atc ggc       206
Lys His Ser Pro Leu Ala Leu Leu Ala Ala Thr Cys Ser Arg Ile Gly
     30                  35                  40 cag ccc ggc gct gcg gcg gca ccc gac ttc ctt cag gtg ccc tat gac       254
Gln Pro Gly Ala Ala Ala Pro Asp Phe Leu Gln Val Pro Tyr Asp
 45                  50                  55                  60 cca gcg ctg ggt tca ccc tcc aga ctt ttc cac cct tgg act gcc gac       302
Pro Ala Leu Gly Ser Pro Ser Arg Leu Phe His Pro Trp Thr Ala Asp
                 65                  70                  75 atg ccc gcg cac tcg cca ggc gcc ctg ccc ccc cac ccc agc ctg           350
Met Pro Ala His Ser Pro Gly Ala Leu Pro Pro Pro His Pro Ser Leu
             80                  85                  90 ggg ctg acg ccg cag aaa aca cac ctg cag ccg tcc ttc ggg gca gcc       398
Gly Leu Thr Pro Gln Lys Thr His Leu Gln Pro Ser Phe Gly Ala Ala
         95                 100                 105 cac gag ctc ccg ctc acg ccc ccc gcg gat ccg tcg tac cct tac gag       446
His Glu Leu Pro Leu Thr Pro Pro Ala Asp Pro Ser Tyr Pro Tyr Glu
    110                 115                 120 ttc tcg ccg gtc aag atg ctg ccc tcg agc atg gct gct ctg cct gcc       494
Phe Ser Pro Val Lys Met Leu Pro Ser Ser Met Ala Ala Leu Pro Ala
125                 130                 135                 140 agc tgc gcg ccc gcc tac gtg ccc tac gcc gcg cag gcc gcg ttg ccc       542
Ser Cys Ala Pro Ala Tyr Val Pro Tyr Ala Ala Gln Ala Ala Leu Pro
                145                 150                 155 ccg ggc tac tcc aac ctg ctg ccc ccg ccg cca ccg cct cca ccg           590
Pro Gly Tyr Ser Asn Leu Leu Pro Pro Pro Pro Pro Pro Pro
                160                 165                 170
```

| | | |
|---|---|---|
| ccc acc tgc cgc cag tta tcc ccc gcc ccg gct ccg gac gac ctc ccc<br>Pro Thr Cys Arg Gln Leu Ser Pro Ala Pro Ala Pro Asp Asp Leu Pro<br>175 180 185 | 638 |
| tgg tgg agc atc ccg caa tcg ggc gcg ggg ccg ggg agc tcc ggg gtt<br>Trp Trp Ser Ile Pro Gln Ser Gly Ala Gly Pro Gly Ser Ser Gly Val<br>190 195 200 | 686 |
| cca ggg acc agc ctc tcc agc gcc tgt gcc gga cct ccc cac gct ccc<br>Pro Gly Thr Ser Leu Ser Ser Ala Cys Ala Gly Pro Pro His Ala Pro<br>205 210 215 220 | 734 |
| cgc ttc cct gcc tca gcc gcc gct gct gca gcg gcg gct gct gcc ctg<br>Arg Phe Pro Ala Ser Ala Ala Ala Ala Ala Ala Ala Ala Ala Ala Leu<br>225 230 235 | 782 |
| caa cgg ggt cta gtg ttg ggc ccg tcg gac ttt gca cag tac cag agc<br>Gln Arg Gly Leu Val Leu Gly Pro Ser Asp Phe Ala Gln Tyr Gln Ser<br>240 245 250 | 830 |
| cag atc gcc gcg ctg ctg cag acc aag gcc ccc ctg gcg gcc acg gcc<br>Gln Ile Ala Ala Leu Leu Gln Thr Lys Ala Pro Leu Ala Ala Thr Ala<br>255 260 265 | 878 |
| agg agg tgc cgc cgc tgc cgc tgc ccc aac tgc cag gcg gct ggc ggt<br>Arg Arg Cys Arg Arg Cys Arg Cys Pro Asn Cys Gln Ala Ala Gly Gly<br>270 275 280 | 926 |
| gcc ccc gag gcg gaa ccg ggc aaa aag aag caa cac gtg tgc cac gtg<br>Ala Pro Glu Ala Glu Pro Gly Lys Lys Lys Gln His Val Cys His Val<br>285 290 295 300 | 974 |
| cca ggc tgt ggc aag gtg tac ggc aaa acg tcg cac ctg aag gcg cac<br>Pro Gly Cys Gly Lys Val Tyr Gly Lys Thr Ser His Leu Lys Ala His<br>305 310 315 | 1022 |
| ctg cgc tgg cac acg ggc gag cgg ccc ttc gtg tgc aac tgg ctc ttc<br>Leu Arg Trp His Thr Gly Glu Arg Pro Phe Val Cys Asn Trp Leu Phe<br>320 325 330 | 1070 |
| tgc ggc aag agc ttc acg cgc tcg gac gag ctg caa cgg cac ctg cgg<br>Cys Gly Lys Ser Phe Thr Arg Ser Asp Glu Leu Gln Arg His Leu Arg<br>335 340 345 | 1118 |
| act cac acg ggc gag aag cgc ttc gct tgt ccc gag tgc ggc aaa cgc<br>Thr His Thr Gly Glu Lys Arg Phe Ala Cys Pro Glu Cys Gly Lys Arg<br>350 355 360 | 1166 |
| ttc atg cga agc gat cac ctc gcc aag cac gtg aag acg cac caa aat<br>Phe Met Arg Ser Asp His Leu Ala Lys His Val Lys Thr His Gln Asn<br>365 370 375 380 | 1214 |
| aag aag ctc aaa gtc gct gag gcc ggg gtg aag cgg gag aat ccg cgg<br>Lys Lys Leu Lys Val Ala Glu Ala Gly Val Lys Arg Glu Asn Pro Arg<br>385 390 395 | 1262 |
| gac cta tgagcgcacc gggacacttt cgaggccact cctgcccaag acatctttcc<br>Asp Leu | 1318 |
| cagcacctttt gctggcacac cagggtactt gccatcgagg tagctgacaa agagtaactt | 1378 |
| tttaaatgaa cttttttattc tcctccgccc gaagtcttgc tgtccagccc aagagcagag | 1438 |
| ggcagggcag gcaggacagg aaactgggtc gtagttgagt tacccccagga ggattccaaa | 1498 |
| gtccgagcca tcgcctgcct gggagactta cattttaccc agggctggcc ttgcttgtgg | 1558 |
| gagtcgctgc tgaaaaaaaa ttttaaaaag aaggctcttg ggagatttaa aaacaaggcc | 1618 |
| taagttttttg ctaggcccga ttcggacttt gtacaggtta tttaataata gctttgttaa | 1678 |
| agagtaatta tgattataac gttaataaat gtttctgttg ttctcagctc cacgcagagc | 1738 |
| tacagcatgg tacgtttctg taaagcgaac agcagttggc agcgtgaaaa taaatacttc | 1798 |
| attccagggt ctcctcggga agaccccccac ag | 1830 |

<210> SEQ ID NO 2
<211> LENGTH: 398
<212> TYPE: PRT
<213> ORGANISM: Mus musculus

<400> SEQUENCE: 2

Met Ala Ala Val Ala Val Leu Arg Asn Asp Ser Leu Gln Ala Phe Leu
1               5                   10                  15

Gln Asp Arg Thr Pro Ser Ala Ser Pro Asp Leu Gly Lys His Ser Pro
            20                  25                  30

Leu Ala Leu Leu Ala Ala Thr Cys Ser Arg Ile Gly Gln Pro Gly Ala
        35                  40                  45

Ala Ala Ala Pro Asp Phe Leu Gln Val Pro Tyr Asp Pro Ala Leu Gly
    50                  55                  60

Ser Pro Ser Arg Leu Phe His Pro Trp Thr Ala Asp Met Pro Ala His
65                  70                  75                  80

Ser Pro Gly Ala Leu Pro Pro His Pro Ser Leu Gly Leu Thr Pro
                85                  90                  95

Gln Lys Thr His Leu Gln Pro Ser Phe Gly Ala Ala His Glu Leu Pro
            100                 105                 110

Leu Thr Pro Pro Ala Asp Pro Ser Tyr Pro Tyr Glu Phe Ser Pro Val
        115                 120                 125

Lys Met Leu Pro Ser Ser Met Ala Ala Leu Pro Ala Ser Cys Ala Pro
    130                 135                 140

Ala Tyr Val Pro Tyr Ala Ala Gln Ala Ala Leu Pro Pro Gly Tyr Ser
145                 150                 155                 160

Asn Leu Leu Pro Pro Pro Pro Pro Pro Pro Pro Thr Cys Arg
                165                 170                 175

Gln Leu Ser Pro Ala Pro Ala Pro Asp Asp Leu Pro Trp Trp Ser Ile
            180                 185                 190

Pro Gln Ser Gly Ala Gly Pro Gly Ser Ser Gly Val Pro Gly Thr Ser
        195                 200                 205

Leu Ser Ser Ala Cys Ala Gly Pro Pro His Ala Pro Arg Phe Pro Ala
    210                 215                 220

Ser Ala Ala Ala Ala Ala Ala Ala Ala Leu Gln Arg Gly Leu
225                 230                 235                 240

Val Leu Gly Pro Ser Asp Phe Ala Gln Tyr Gln Ser Gln Ile Ala Ala
                245                 250                 255

Leu Leu Gln Thr Lys Ala Pro Leu Ala Ala Thr Ala Arg Arg Cys Arg
            260                 265                 270

Arg Cys Arg Cys Pro Asn Cys Gln Ala Ala Gly Gly Ala Pro Glu Ala
        275                 280                 285

Glu Pro Gly Lys Lys Lys Gln His Val Cys His Val Pro Gly Cys Gly
    290                 295                 300

Lys Val Tyr Gly Lys Thr Ser His Leu Lys Ala His Leu Arg Trp His
305                 310                 315                 320

Thr Gly Glu Arg Pro Phe Val Cys Asn Trp Leu Phe Cys Gly Lys Ser
                325                 330                 335

Phe Thr Arg Ser Asp Glu Leu Gln Arg His Leu Arg Thr His Thr Gly
            340                 345                 350

Glu Lys Arg Phe Ala Cys Pro Glu Cys Gly Lys Arg Phe Met Arg Ser
        355                 360                 365

Asp His Leu Ala Lys His Val Lys Thr His Gln Asn Lys Lys Leu Lys
    370                 375                 380

-continued

```
Val Ala Glu Ala Gly Val Lys Arg Glu Asn Pro Arg Asp Leu
385                 390                 395

<210> SEQ ID NO 3
<211> LENGTH: 1197
<212> TYPE: DNA
<213> ORGANISM: Homo sapiens
<220> FEATURE:
<221> NAME/KEY: CDS
<222> LOCATION: (1)..(1194)

<400> SEQUENCE: 3 atg gcc gcg gtg gcc gtc ctc cgg aac gac tcg ctg cag gcc ttt ctc      48
Met Ala Ala Val Ala Val Leu Arg Asn Asp Ser Leu Gln Ala Phe Leu
  1               5                  10                  15 cag gac cgc acc ccc agc gcc tcc ccg gac ctg ggc aag cac tcg ccc      96
Gln Asp Arg Thr Pro Ser Ala Ser Pro Asp Leu Gly Lys His Ser Pro
             20                  25                  30 ctg gca ttg ctg gcc gcc acc tgt agc cgc atc ggc cag ccg ggc gcg     144
Leu Ala Leu Leu Ala Ala Thr Cys Ser Arg Ile Gly Gln Pro Gly Ala
         35                  40                  45 gcg gcg ccc ccg gac ttc ctg cag gtg ccc tac gac ccc gcg ctg ggc     192
Ala Ala Pro Pro Asp Phe Leu Gln Val Pro Tyr Asp Pro Ala Leu Gly
     50                  55                  60 tca ccc tcc agg ctc ttc cac ccg tgg acc gcc gac atg ccg gcg cac     240
Ser Pro Ser Arg Leu Phe His Pro Trp Thr Ala Asp Met Pro Ala His
 65                  70                  75                  80 tcg cca ggc gca ctg ccg ccc ccg cat ccc agc ttg ggg ctg acg ccg     288
Ser Pro Gly Ala Leu Pro Pro Pro His Pro Ser Leu Gly Leu Thr Pro
                 85                  90                  95 cag aag acg cac ctg cag ccg tcc ttc ggg gct gcg cac gag ctt ccc     336
Gln Lys Thr His Leu Gln Pro Ser Phe Gly Ala Ala His Glu Leu Pro
            100                 105                 110 ctt aca ccc ccc gcc gac ccc tcg tac ccc tac gag ttc tcg ccg gtc     384
Leu Thr Pro Pro Ala Asp Pro Ser Tyr Pro Tyr Glu Phe Ser Pro Val
        115                 120                 125 aag atg ctg ccc tcg agc atg gcg gct ctg ccc gcc agc tgc gcg ccc     432
Lys Met Leu Pro Ser Ser Met Ala Ala Leu Pro Ala Ser Cys Ala Pro
    130                 135                 140 gcc tac gtg ccc tac gcg gcg cag gcc gcg ctg ccg cca ggc tac tcc     480
Ala Tyr Val Pro Tyr Ala Ala Gln Ala Ala Leu Pro Pro Gly Tyr Ser
145                 150                 155                 160 aac ctg ctg cct ccg ccg ccg ccg ccg ccg ccc acc tgc cgc     528
Asn Leu Leu Pro Pro Pro Pro Pro Pro Pro Pro Thr Cys Arg
                165                 170                 175 cag ttg tca ccc aac ccg gcc ccc gac gac ctc ccg tgg tgg agc atc     576
Gln Leu Ser Pro Asn Pro Ala Pro Asp Asp Leu Pro Trp Trp Ser Ile
            180                 185                 190 ccg cag gcg ggc gcc ggg ccg ggg gcc tcc ggg gtt ccg gga agc ggc     624
Pro Gln Ala Gly Ala Gly Pro Gly Ala Ser Gly Val Pro Gly Ser Gly
        195                 200                 205 ctc tcc ggc gcc tgt gcc ggg gcc ccc cac gcg ccc cgc ttc ccc gcc     672
Leu Ser Gly Ala Cys Ala Gly Ala Pro His Ala Pro Arg Phe Pro Ala
    210                 215                 220 tct gcg gcc gct gct gct gcg gcc gcc gcc cta caa aga ggc ctg     720
Ser Ala Ala Ala Ala Ala Ala Ala Ala Ala Leu Gln Arg Gly Leu
225                 230                 235                 240 gtg ttg ggc ccg tcg gac ttt gcg cag tac cag agc cag atc gcc gcg     768
Val Leu Gly Pro Ser Asp Phe Ala Gln Tyr Gln Ser Gln Ile Ala Ala
                245                 250                 255 ctg ctg cag acc aag gcc ccc ctg gcg gcc acg gcc agg agg tgc cgc     816
```

```
Leu Leu Gln Thr Lys Ala Pro Leu Ala Ala Thr Ala Arg Arg Cys Arg
            260                 265                 270 cgc tgc cgc tgt ccc aac tgc cag gcg gcg ggc ggc gcc ccc gag gcg    864
Arg Cys Arg Cys Pro Asn Cys Gln Ala Ala Gly Gly Ala Pro Glu Ala
        275                 280                 285 gag ccg ggg aag aag aag cag cac gtg tgc cac gtg ccg ggc tgc ggc    912
Glu Pro Gly Lys Lys Lys Gln His Val Cys His Val Pro Gly Cys Gly
    290                 295                 300 aag gtg tac ggg aag acg tcg cac ctg aag gcg cac ctg cgc tgg cac    960
Lys Val Tyr Gly Lys Thr Ser His Leu Lys Ala His Leu Arg Trp His
305                 310                 315                 320 acg ggc gag cga ccc ttc gtg tgc aac tgg ctc ttc tgc ggg aag agc    1008
Thr Gly Glu Arg Pro Phe Val Cys Asn Trp Leu Phe Cys Gly Lys Ser
                325                 330                 335 ttc acg cgc tcg gac gag ctg cag cgg cac ctg cgg act cac acg ggc    1056
Phe Thr Arg Ser Asp Glu Leu Gln Arg His Leu Arg Thr His Thr Gly
            340                 345                 350 gag aag cgc ttt gcc tgt ccc gag tgc ggc aag cgc ttc atg cgc agc    1104
Glu Lys Arg Phe Ala Cys Pro Glu Cys Gly Lys Arg Phe Met Arg Ser
        355                 360                 365 gac cac ctc gcg aag cac gtc aag act cac cag aat aag aag ctc aaa    1152
Asp His Leu Ala Lys His Val Lys Thr His Gln Asn Lys Lys Leu Lys
    370                 375                 380 gtc gct gag gcc ggg gtt aag cgg gag gac gcg cgg gac ctg tga        1197
Val Ala Glu Ala Gly Val Lys Arg Glu Asp Ala Arg Asp Leu
385                 390                 395

<210> SEQ ID NO 4
<211> LENGTH: 398
<212> TYPE: PRT
<213> ORGANISM: Homo sapiens

<400> SEQUENCE: 4

Met Ala Ala Val Ala Val Leu Arg Asn Asp Ser Leu Gln Ala Phe Leu
 1               5                  10                  15

Gln Asp Arg Thr Pro Ser Ala Ser Pro Asp Leu Gly Lys His Ser Pro
            20                  25                  30

Leu Ala Leu Leu Ala Ala Thr Cys Ser Arg Ile Gly Gln Pro Gly Ala
        35                  40                  45

Ala Ala Pro Pro Asp Phe Leu Gln Val Pro Tyr Asp Pro Ala Leu Gly
    50                  55                  60

Ser Pro Ser Arg Leu Phe His Pro Trp Thr Ala Asp Met Pro Ala His
65                  70                  75                  80

Ser Pro Gly Ala Leu Pro Pro His Pro Ser Leu Gly Leu Thr Pro
                85                  90                  95

Gln Lys Thr His Leu Gln Pro Ser Phe Gly Ala Ala His Glu Leu Pro
            100                 105                 110

Leu Thr Pro Pro Ala Asp Pro Ser Tyr Pro Tyr Glu Phe Ser Pro Val
        115                 120                 125

Lys Met Leu Pro Ser Ser Met Ala Ala Leu Pro Ala Ser Cys Ala Pro
    130                 135                 140

Ala Tyr Val Pro Tyr Ala Ala Gln Ala Ala Leu Pro Pro Gly Tyr Ser
145                 150                 155                 160

Asn Leu Leu Pro Pro Pro Pro Pro Pro Pro Pro Pro Thr Cys Arg
                165                 170                 175

Gln Leu Ser Pro Asn Pro Ala Pro Asp Asp Leu Pro Trp Trp Ser Ile
            180                 185                 190
```

-continued

```
Pro Gln Ala Gly Ala Gly Pro Gly Ala Ser Gly Val Pro Gly Ser Gly
        195                 200                 205

Leu Ser Gly Ala Cys Ala Gly Ala Pro His Ala Pro Arg Phe Pro Ala
        210                 215                 220

Ser Ala Ala Ala Ala Ala Ala Ala Ala Leu Gln Arg Gly Leu
225                 230                 235                 240

Val Leu Gly Pro Ser Asp Phe Ala Gln Tyr Gln Ser Gln Ile Ala Ala
            245                 250                 255

Leu Leu Gln Thr Lys Ala Pro Leu Ala Ala Thr Ala Arg Arg Cys Arg
            260                 265                 270

Arg Cys Arg Cys Pro Asn Cys Gln Ala Gly Gly Ala Pro Glu Ala
        275                 280                 285

Glu Pro Gly Lys Lys Gln His Val Cys His Val Pro Gly Cys Gly
        290                 295                 300

Lys Val Tyr Gly Lys Thr Ser His Leu Lys Ala His Leu Arg Trp His
305                 310                 315                 320

Thr Gly Glu Arg Pro Phe Val Cys Asn Trp Leu Phe Cys Gly Lys Ser
                325                 330                 335

Phe Thr Arg Ser Asp Glu Leu Gln Arg His Leu Arg Thr His Thr Gly
            340                 345                 350

Glu Lys Arg Phe Ala Cys Pro Glu Cys Gly Lys Arg Phe Met Arg Ser
        355                 360                 365

Asp His Leu Ala Lys His Val Lys Thr His Gln Asn Lys Lys Leu Lys
        370                 375                 380

Val Ala Glu Ala Gly Val Lys Arg Glu Asp Ala Arg Asp Leu
385                 390                 395

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 5
tgtaaaacga cggccagt                                                        18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 6
caggaaacag ctatgacc                                                        18

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 7
cagccctggg taaaatgtaa gtc                                                  23
```

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 8
tcgaggtagc tgacaaagag taac                                          24

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 9
tcaccagtgc agggatctac aaa                                           23

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 10
gcagtcaggt gtcttggtct gatt                                          24

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 11
taatacgact cactataggg                                               20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 12
atttaggtga cactataga                                                19

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 13
ttctcgcccg tgtgagtccg ca                                            22

<210> SEQ ID NO 14

-continued

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 14
tccagacttt tccacccttg gact                                          24

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 15
gagattgttg ccatcaacga cc                                            22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 16
gttgaagtcg caggagacaa cc                                            22

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 17
ctttgcrcag taccagagcc agat                                          24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 18
aagaagaagc agcacgtgtg ccac                                          24

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 19
ggcgtcccgc tccgcagcca                                               20

<210> SEQ ID NO 20
<211> LENGTH: 23
```

```
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 20
ccggcctcag cgactttgag ctt                                        23

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 21
gaattccctt caagcagtag ccatggccg                                  29

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 22
gaattccttt gcataccaga gcgagat                                    27

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 23
gtcgacatct ggctctggta ctgtgcaaag                                 30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 24
gtcgacagtg tcccggtgcg ctcataggtc                                 30

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 25
tcgaaaggag gcgggacccg agct                                       24

<210> SEQ ID NO 26
<211> LENGTH: 25
<212> TYPE: DNA
```

```
<213> ORGANISM: Artificial Sequence
<220> FEATURE:
<223> OTHER INFORMATION: Description of Artificial Sequence:Artificially
      Synthesized Primer Sequence

<400> SEQUENCE: 26
tcgaaaggag ttttgacccg gagct                                          25
```